United States Patent [19]

McCaulay

[11] 4,300,008

[45] Nov. 10, 1981

[54] PREPARATION OF 2,6-DIMETHYLDECALIN AND ITS ISOMERS

[75] Inventor: David A. McCaulay, Homewood, Ill.

[73] Assignee: Standard Oil Company (Indiana), Chicago, Ill.

[21] Appl. No.: 190,621

[22] Filed: Sep. 25, 1980

[51] Int. Cl.³ .................. C07C 2/76; C07C 13/28; C07C 175/00

[52] U.S. Cl. .................. 585/360; 585/362; 208/134

[58] Field of Search .................. 585/360, 362

[56] References Cited

U.S. PATENT DOCUMENTS

| | | | |
|---|---|---|---|
| 3,708,553 | 1/1973 | Olah | 585/455 |
| 3,728,411 | 4/1973 | Siskin et al. | 585/464 |
| 3,766,286 | 10/1973 | Olah | 585/480 |
| 4,098,833 | 7/1978 | Wristers | 585/464 |
| 4,105,704 | 8/1978 | Say et al. | 585/464 |
| 4,116,880 | 9/1978 | Olah | 585/462 |

*Primary Examiner*—Curtis R. Davis
*Attorney, Agent, or Firm*—James R. Henes; William T. McClain; William H. Magidson

[57] ABSTRACT

Methods employing a catalyst system comprising a hydrogen fluoride solution of tantalum pentafluoride and/or niobium pentafluoride for the preparation of 2,6-dimethyldecalin from a 12 carbon atom-containing dicyclic naphthenic isomer thereof and for the preparation of a mixture of 2,6-dimethyldecalin and a 12 carbon atom-containing dicyclic naphthenic isomer thereof from methylcyclopentane and/or cyclohexane are disclosed.

29 Claims, 3 Drawing Figures

PREPARATION OF 2,6-DIMETHYLDECALIN AND ITS ISOMERS

BACKGROUND OF THE INVENTION

1. Field of the Invention

In one respect, this invention relates generally to a method for the preparation of 2,6-dimethyldecalin from a 12 carbon atom-containing dicyclic naphthenic isomer thereof. In another respect, this invention relates generally to a method for the preparation of a mixture of 2,6-dimethyldecalin and a 12 carbon atom-containing dicyclic naphthenic isomer thereof. More particularly this invention concerns the aforesaid methods employing in each a catalyst system comprising a hydrogen fluoride solution of tantalum pentafluoride and/or niobium pentafluoride.

2. Description of the Prior Art

Dimethyldecalins (dimethyldecahydronaphthalenes) are useful intermediates for the preparation of various intermediates containing functional groups. Particularly, dimethyldecalins can be dehydrogenated to form dimethylnaphthalenes which can be oxidized under controlled conditions, as exemplified by Saffer et al., U.S. Pat. No. 2,833,816, to form the corresponding dicarboxylic acids. A naphthalene dicarboxylic acid in which the carboxyl groups are located at the 2.6 positions is a highly desirable article of commerce, particularly in that it can be used for making polyester-type resins which have outstanding properties in various applications.

A difficulty in the commercial preparation of 2,6-naphthalene dicarboxylic acid lies in finding a suitable source of 2,6-dimethylnaphthalene. This compound occurs in coal tar and cracked petroleum fractions of appropriate boiling range but only in low concentrations since it is associated with the various other dimethylnaphthalene isomers, monocyclic aromatics, and non-aromatic hydrocarbons. A concentrate of the dimethylnaphthalene isomers can be obtained by solvent extraction of the fraction with an aromatic-selective solvent such as furfural, but the 2,6-isomer is still only a minor constituent of the concentrate. Attempts to isomerize the other isomers, particularly those in which both methyl groups are positioned on the same ring, to produce only the 2,6-isomer have not been successful.

Consequently, the preparation of 2,6-dimethyldecalin for use as an intermediate in the preparation of 2,6-dimethylnaphthalene has received considerable attention. For example, Schneider, U.S. Pat. No. 3,243,469 discloses a method for the preparation of 2,6-dimethyldecalins by isomerization of any dicyclic naphthene of 12 carbon atoms utilizing a catalyst system of aluminum halide and hydrogen halide at a temperature of $-10°$ C. to 60° C. The isomerization product is an equilibrium mixture of dimethyldecalins including 2,6-dimethyldecalin. After removal of the catalyst, 2,6-dimethyldecalin can be separated from the equilibrium mixture by fractional crystallization at a temperature below $-10°$ C. The other isomers can be recycled to the isomerization step for further equilibration, to ultimately convert essentially all of the original dicyclic naphthenes being converted to 2,6-dimethyldecalin.

Schneider, U.S. Pat. No. 3,346,656, discloses a method for preparing dimethyldecalins from naphthenes of 6 carbon atoms in which a naphthene of 6 carbon atoms or a mixture of such naphthenes is contacted at a temperature in the range of $-20°$ C. to 80° C. with a preformed liquid catalyst complex obtained by reacting a paraffin hydrocarbon having at least 8 carbon atoms per molecule with $AlCl_3$-HCl or $AlBr_3$-HBr. Under these conditions, the naphthene of 6 carbon atoms dimerizes to form a dicyclic naphthene of 12 carbon atoms which isomerizes to an equilibrium mixture of dimethyldecalins. Schneider, U.S. Pat. No. 3,219,718, discloses a method for the preparation of decalins by the rearrangement of uncondensed dicyclic naphthenes having 2 cyclohexyl rings utilizing an aluminum halide-hydrogen halide catalyst. This patent discloses that any uncondensed dicyclic naphthene having 12-20 carbon atoms and 2 cyclohexyl rings in the presence of such catalyst at a temperature in the range of $-20°$ C. to 70° C. will rearrange to form decalins having the same empirical formula as the dicyclic naphthene. The decalins formed when relatively long reaction times are used are an equilibrium mixture of isomers having the same number of carbon atoms per molecule as the dicyclic naphthene used as the starting material.

Suld et al., U.S. Pat. No. 3,200,161 disclose another method by which any dicyclic naphthene containing 12 carbon atoms can be isomerized to 2,6-dimethyldecalin. The naphthene rings of the starting material can be either condensed or noncondensed, and any alkyl substituent or substituents can be included that will result in the naphthene having 12 carbon atoms. Disclosed means for obtaining such starting materials include separation from suitable petroleum fractions, hydrogenation of coal tar fractions, and dimerization of methylcyclopentane and/or cyclohexane. In the disclosed method, the dicyclic naphthene is contacted with a catalyst containing hydrogen fluoride, a promoter, and an initiator at a temperature in the range of $-10°$ C. to $-60°$ C. The promoter can be either boron trifluoride or an antimony pentafluoride. The initiator can be any olefin, alcohol, ether, or alkyl halide containing not more than 5 carbon atoms. Within a short time interval after isomerization commences, 2,6-dimethyldecalin begins to precipitate. Thereafter, isomerization and precipitation occur simultaneously and continue until over 50 weight percent of the starting material has been recovered as solid 2,6-dimethyldecalin.

A method disclosed in abandoned patent application Ser. No. 69,798 filed Nov. 17, 1960 has also been reported in the aforesaid Suld et al., U.S. Pat. No. 3,200,161, according to which any dicyclic naphthene containing 12 carbon atoms can be isomerized to an equilibrium mixture of dimethyldecalins in which 2,6-dimethyldecalin occurs in relatively high proportion. The method comprises contacting the dicyclic naphthene with an aluminum bromide-hydrogen bromide catalyst at a temperature in the range of from about 10° C. to 60° C. 2,6-Dimethyldecalin can be separated from the resulting equilibrium mixture by cooling the mixture to about $-20°$ C. to $-40°$ C., for within this temperature range the 2,6-isomer selectively crystallizes, the other isomers remaining in the liquid phase.

Bushick et al., U.S. Pat. No. 3,509,223, disclose a method for dimerizing monocyclic naphthenes in the presence of a catalyst system and a suitable hydrogen acceptor. Any naphthene containing 6 carbon atoms is suitable for use as a charge stock in such method. The catalyst system employed for the dimerization consists of hydrogen fluoride, boron trifluoride, and a hydride acceptor-chain initiator. The hydride acceptor-initiator is an organic compound containing less than 6 carbon atoms, which is generally an olefin or an alkyl halide, although alcohols and ethers are also functional. In accordance with such method, the naphthene or a mixture of such naphthenes is contacted at a temperature in the range of −20° C. to 80° C. with the catalyst system. Under these conditions, the naphthene dimerizes to form a dicyclic napthene containing 12 carbon atoms, which then isomerizes to form an equilibrium mixture of dimethyldecalins. The equilibrium mixtures contain approximately 30 percent each of 2,6- and 2,7-dimethyldecalins.

A major problem in each of the aforesaid prior art methods is that the relative yield of 2,6-dimethyldecalin is low and/or that the method is a multi-step method and/or that a promoter and/or initiator is required for the reaction. The initiators or promoters conventionally used in the aforesaid prior art methods generally have the side effect of acting as a catalyst poison and hence of shortening useful catalyst life. Such problems can be overcome by the method of this invention which, unlike the aforesaid prior art methods, employs a catalyst system of tantalum or niobium pentafluoride in hydrogen fluoride.

Hydrocarbon conversion processes involving the use of catalysts comprising tantalum or niobium pentafluoride in hydrogen fluoride have been extensively described in the prior art. For example, Lien et al., U.S. Pat. Nos. 2,683,763 and 2,683,764 disclose that the combination of hydrogen fluoride with either tantalum pentafluoride or niobium pentafluoride are powerful catalysts for isomerization, alkylation, cracking and other reactions. Oelderik et al., U.S. Pat. No. 3,201,494 disclose that niobium pentafluoride or tantalum pentafluoride in combination with hydrofluoric acid can be employed for the isomerization of hexane. McCaulay et al., U.S. Pat. No. 4,214,116 and U.S. patent application Ser. No. 47,059 filed on June 11, 1979 and now U.S. Pat. No. 4,246,094, disclose improved processes for isomerizing and improving the octane rating of hydrocarbons in the naphtha boiling range.

Siskin et al., U.S. Pat. No. 3,852,184, disclose a process for upgrading reformer feedstocks containing alkylcyclopentanes by isomerizing the feedstock components in the presence of a catalyst mixture containing a metal halide, such as tantalum and/or niobium pentafluoride, and a protonic acid, such as hydrogen fluoride, and preferably in the presence of hydrogen, at a temperature in the range of −30° C. to 125° C., so that the alkylcyclopentanes are converted to the corresponding cyclohexane isomers. Siskin et al., U.S. Pat. No. 3,948,761 disclose a method for isomerizing acyclic and alicyclic aliphatic hydrocarbons by contacting the same with hydrogen in the presence of a difficultly reducible metal halide, such as tantalum pentafluoride, niobium pentafluoride, or their mixtures, in combination with at least a molar equivalent of hydrogen halide. Typically, acyclic hydrocarbons having at least 4 carbon atoms, that is, straight chain or branched chain paraffins having from 4 to 10 carbon atoms, are converted to branched materials having higher octane ratings. Additionally, alicyclic hydrocarbons having at least about 5 carbon atoms, such as cyclohexane, can be converted to isomers thereof by the same method. This hydroisomerization is performed at temperatures in the range of from about 0° C. to about 150° C. The patentees of U.S. Pat. Nos. 3,852,184 and 3,948,761 do not disclose dimerization of methylcyclopentane or cyclohexane to form 12 carbon atom-containing dicyclic naphthenes such as dimethyldecalins. In fact, analysis of the products of the specific examples in these patents indicated a net decrease in the concentration of dicyclic naphthenes from that in the reactants. Furthermore, the patentees disclose that the presence of sulfur compounds or aromatics does not adversely effect the catalyst. In each of the specific examples, substantial quantities of aromatics and/or sulfur compounds are present. The examples of U.S. Pat. No. 3,948,761 also employ feeds in which the concentration of methylcyclopentane and/or cyclohexane is too low, according to the present invention, for dimerization to occur.

However, thus far a catalyst system comprising tantalum pentafluoride or niobium pentafluoride in hydrogen fluoride has not been employed in a method for preparing 2,6-dimethyldecalin from its 12 carbon atom-containing dicyclic naphthenic isomers or for preparing mixtures of 2,6-dimethyldecalin and its 12 carbon atom-containing dicyclic naphthenic isomers as dimerization products.

OBJECTS OF THE INVENTION

It is therefore a general object of the present invention to provide an improved method for preparing 2,6-dimethyldecalin which overcomes the problems of the prior art methods.

More particularly, it is an object of the present invention to provide a method for preparing 2,6-dimethyldecalin in high yield.

Another object of the present invention is to provide a catalytic method for preparing 2,6-dimethyldecalin utilizing a catalyst which is capable of having a long useful life.

A further object of the present invention is to provide a method for preparing and separating 2,6-dimethyldecalin from isomeric dicyclic naphthenes containing 12 carbon atoms which is capable of being performed in a single step.

A related object of the present invention is to provide a method for preparing mixtures of 2,6-dimethyldecalin and 12 carbon atom-containing dicyclic naphthenic isomers thereof which can in turn be converted to 2,6-dimethyldecalin.

More particularly, it is an object of the present invention to provide a method for preparing from naturally occurring feedstocks containing relatively minor amounts of methylcyclopentane and cyclohexane or dicyclic naphthenes of 12 carbon atoms, a concentrated solution of dicyclic naphthenes of 12 carbon atoms which can then be isomerized to 2,6-dimethyldecalin.

Other objects and advantages of the invention will become apparent upon reading the following detailed description and appended claims and upon reference to the accompanying drawings.

SUMMARY OF THE INVENTION

In one respect the present invention is a process for preparing 2,6-dimethyldecalin comprising contacting one or more 12 carbon atom-containing dicyclic naphthenic isomers of 2,6-dimethyldecalin with an isomerization catalyst system comprising a solution of tantalum or niobium pentafluoride or both in hydrogen fluoride at a temperature in the range of from about −60° C. to about 90° C. and in the presence of hydrogen, to thereby isomerize the dicyclic naphthenic isomer to 2,6-dimethyldecalin. The use of the aforesaid isomerization catalyst system permits a high yield of 2,6-dimethyldecalin and does not require a promoter or initiator.

Furthermore, under certain conditions, 2,6-dimethyldecalin can be formed and separated in a single step by the method of the present invention.

In another respect, the present invention is a process for preparing at least one 12 carbon atom-containing dicyclic naphthene comprising contacting a hydrocarbon solution comprising at least 40 to 100 weight percent of methylcyclopentane, cyclohexane or both with a dimerization catalyst system comprising a solution of tantalum pentafluoride or niobium pentafluoride or both in hydrogen fluoride at a temperature in the range of from about 10° C. to about 90° C. and in the presence of hydrogen at a partial pressure in the range of from about 0.7 to about 20 atmospheres, the hydrocarbon solution being substantially free of amounts of sulfur-containing compounds and aromatic and other unsaturated organic compounds sufficient to deactivate the dimerization catalyst system. The weight ratio of the pentafluoride to the hydrogen fluoride in the aforesaid dimerization catalyst system is in the range of from about 0.1 to about 2, to thereby dimerize the methylcyclopentane or cyclohexane or both to at least one of the aforesaid dicyclic naphthenes. Outside of the aforesaid ranges of concentration of methylcyclopentane and/or cyclohexane, hydrogen partial pressures, weight ratio of the pentafluoride to hydrogen fluoride and without the absence of interfering amounts of sulfur-containing compounds and aromatic and other unsaturated organic compounds, methylcyclopentane and cyclohexane do not undergo dimerization but merely undergo cracking and isomerization reactions.

BRIEF DESCRIPTION OF THE DRAWINGS

For a more complete understanding of this invention, reference should now be made to the embodiments illustrated in greater detail in the accompanying drawings and described below by way of examples of the invention. In the drawings.

DETAILED DESCRIPTION OF THE DRAWINGS INCLUDING PREFERRED EMBODIMENTS

Figure 1:
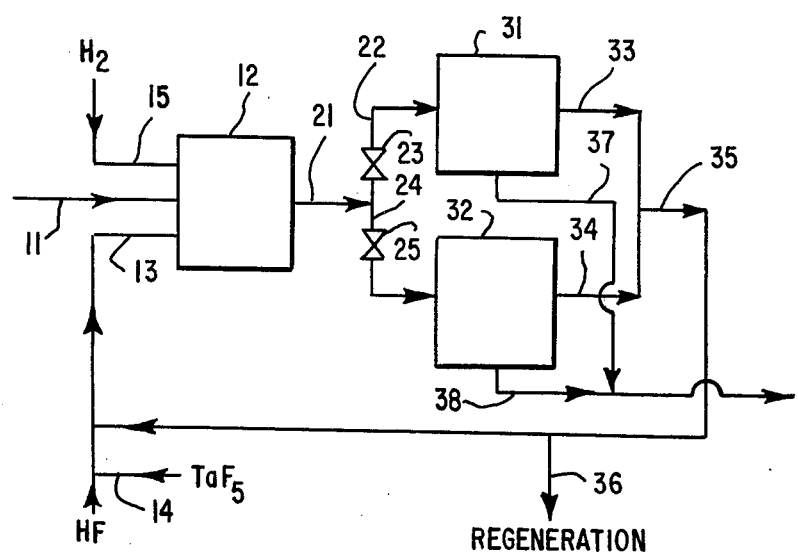
FIG. 1 is a schematic illustration of one preferred embodiment of the method of this invention in which at least one 12 carbon atom-containing dicyclic naphthenic isomer of 2,6-dimethyldecalin in a feed stream is continuously and catalytically isomerized to 2,6-dimethyldecalin, and simultaneously 2,6-dimethyldecalin originally present in the feed stream and 2,6-dimethyldecalin being formed by the isomerization are precipitated.

Preparation of 2,6-Dimethyldecalin From Dicyclic Naphthenic Isomers Thereof

In one respect, this invention involves a method for the catalyzed isomerization of a 12 carbon atom-containing dicyclic naphthenic isomer of 2,6-dimethyldecalin to 2,6-dimethyldecalin. The naphthene rings of the starting material can be either condensed or noncondensed, and any alkyl substituent or substituents can be included that will result in the dicyclic naphthene having 12 carbon atoms. The starting material thus can comprise one or more of the ethyldecalins, bicyclohexyl, the dimethylbicyclopentyls, the ethylbicyclopentyls, 1,2-dicyclopentylethane, the cyclopentylmethylcyclopentylmethanes, the trimethylhydrindanes, the ethylmethylhydrindanes, the propylhydrindanes, the dimethyldecalin isomers of 2,6-dimethyldecalin, etc.

If other materials are present in the feed to the isomerization reaction in addition to the 12 carbon atom-containing dicyclic naphthene(s) the total concentration of the 12 carbon atom-containing dicyclic naphthenic starting material is preferably high in order to facilitate formation and crystallization of the 2,6-dimethyldecalin. Excessive amounts of a diluent material could serve as an effective solvent for the 2,6-dimethyldecalin and thereby hinder its crystallization from solution. Furthermore, the presence of certain such diluent materials at high concentrations could interfere with the formation of the 2,6-dimethyldecalin. For these reasons, while a total concentration of at least about 5 weight percent of the dicyclic starting materials in the feed is suitable, it is preferred that there be a total concentration of at least about 80 weight percent, more preferably at least about 85 weight percent, of the aforesaid dicyclic naphthenic starting materials in the feed. Since a feed containing such a high concentration of 12 carbon atom-containing dicyclic naphthenes would otherwise be difficult and expensive to obtain, methods for producing such feeds comprising either (1) dimerizing methylcyclopentane and/or cyclohexane in readily available solutions thereof to form 12 carbon atom-containing dicyclic naphthenes and thereafter concentrating the dicyclic naphthenes formed or (2) concentrating 12 carbon atom-containing dicyclic naphthenes present at a level of at least about 5 weight percent in readily available hydrocarbon fractions, are desirable and are described herein below.

Furthermore, sulfur-containing compounds and aromatic and other unsaturated hydrocarbons form complexes with the catalyst system and hasten deactivation of the catalyst system. Consequently, unless its contents of sulfur-containing compounds and of aromatic and other unsaturated hydrocarbons are sufficiently low, preferably the feed to the method of this invention is hydrogenated and desulfurized or the unsaturated and sulfur-containing materials are otherwise removed from the feed. Preferably, the feed contains less than about 50 parts per million by weight of sulfur-containing compounds, and less than about 2.5 percent by weight of aromatics and less than about 0.1 percent by weight of other unsaturated organic compounds. Typically, preferred feeds having the aforesaid preferred low contents of sulfur-containing compounds and of aromatic and other unsaturated organic compounds, boil in the range of from about 210° C., preferably from about 215° C., to about 230° C., preferably to about 225° C.

Sources of starting materials for the isomerization include suitable petroleum fractions or coal tar fractions, etc. A particularly suitable starting material is bicyclohexyl, since it can readily be obtained by dimerizing benzene to form biphenyl which can then be hydrogenated to bicyclohexyl. One source of a hydrocarbon fraction containing a high total concentration of dicyclic naphthenes containing 12 carbon atoms is the high boiling portion of the product from the catalytic reforming of petroleum hydrocarbons. A suitable feed can be obtained by fractionating such high boiling portion of the reformate to separate the fraction thereof containing dicyclic aromatic compounds containing 12 carbon atoms and preferably hydrogenating this fraction to convert the aromatics to the corresponding naphthenes. The reformate fraction is already sufficiently low in sulfur content and need not be desulfurized for preferred operation. The concentration of the aforesaid dicyclic naphthenes can be maximized by performing the fractionation so as to separate a fraction whose boiling point range is only large enough to include the lowest and highest boiling points of the dimethylnaphthalene isomers in the reformate. A particularly suitable fraction of reformate boiling in the range of from about 240° C., preferably from about 250° C., to about 280° C., preferably to about 265° C. (before hydrogenation), can be used.

The isomerization catalyst system employed is a liquid solution of tantalum or niobium pentafluoride in substantially anhydrous hydrogen fluoride. In the present context, tantalum or niobium pentafluoride is meant to include the pentafluoride as well as other fluoride species such as the ions $M_2F_{11}^-$, $M_3F_{16}^-$ and the like that may be formed when the metal pentafluoride is mixed with hydrogen fluoride and the other components of the hydrocarbon fraction. In the above formulae, M represents tantalum or niobium. Tantalum or niobium pentafluoride is also meant to include tantalum or niobium pentafluoride formed in situ as well as other species produced by the reaction of tantalum or niobium pentachloride or similar precursor with hydrogen fluoride. As described hereinbelow, hydrogen is also employed, and, since niobium is more readily reduced by hydrogen than is tantalum from its catalytically active +5 oxidation state to its catalytically inactive +3 oxidation state, tantalum pentafluoride is preferred.

The isomerization is performed at temperatures within the range of from temperatures which are sufficiently high to permit isomerization at a reasonably rapid rate to temperatures which are sufficiently low to enable crystallization of 2,6-dimethyldecalin, but not low enough to permit other components of the reaction mixture to crystallize. Suitably the temperature is in the range of from about −60° C. to about 90° C.

When the temperature is above −10° C., the 2,6-dimethyldecalin formed remains in solution and can be crystallized subsequently by lowering the temperature to below −10° C. Under these conditions, the 2,6 isomer precipitates in substantially pure form and to the substantial exclusion of the other dimethyldecalin isomers. Crystallization of the 2,6-dimethyldecalin shifts the equilibrium between 2,6-dimethyldecalin and its isomers toward the formation of additional 2,6-dimethyldecalin until at least about 85 weight percent of the total amount of 2,6-dimethyldecalin and its isomers is in the form of 2,6-dimethyldecalin. In the alternative and preferably, the isomerization is performed at temperatures below −10° C., and the 2,6-dimethyldecalin crystallizes as it is formed.

The isomerization can be performed batchwise or continuously. In either case, the relative amounts of the feed (reactant or solution containing the reactant) and the metal pentafluoride in the isomerization catalyst system and the contact time of the feed to the catalyst system can be conveniently expressed in terms of weight hourly space velocity (WHSV), in units of grams of feed per gram of the metal pentafluoride per hour of contact time. The WHSV is a function of catalyst activity and suitably is in the range of from about 0.1, preferably from about 0.4, to about 2.0, preferably to about 1.5 grams of feed per gram of metal pentafluoride in the catalyst per hour. Generally, operation at lower temperatures requires the use of correspondingly lower space velocities and at temperatures, for example, at temperatures below −10° C., the WHSV is preferably in the range of from about 0.1, more preferably from about 0.3, to about 0.5, more preferably to about 0.4, grams of feed per gram of metal pentafluoride in the catalyst per hour.

The weight ratio of metal pentafluoride to hydrogen fluoride suitably is in the range of from about 0.1, preferably from about 0.2, to about 2.0, preferably to about 1.2, sufficiently high to achieve the desired activity and rate of reaction and sufficiently low to permit solubilization of the metal pentafluoride. Because of the lower solubility of the metal pentafluoride in hydrogen fluoride at the lower temperatures within the above-described range of isomerization temperatures relative to its solubility at the relatively higher temperatures within the above-described range of isomerization temperatures, lower weight ratios of the pentafluoride to hydrogen fluoride in the range of from about 0.1, preferably from about 0.2, to about 0.5, preferably to about 0.4, are preferably employed when the isomerization temperature is in the range of from −60° C. to −10° C.

Hydrogen is employed to inhibit cracking reactions and the formation of unsaturates which lead to formation of the unsaturated "red oil" which forms a complex which deactivates the catalyst. However, high hydrogen pressures reduce the overall rate of the isomerization reaction. Thus, the hydrogen partial pressure is preferably selected to achieve a balance between reaction rate and catalyst life and preferably is in the range of from about 0.07, more preferably from about 0.34, to about 82, more preferably to about 20 atmospheres. The total pressure under which the isomerization is performed is maintained at a high enough level so that the reaction mixture and catalyst system are substantially in the liquid state.

Gradual deactivation of the metal pentafluoride catalyst caused by the formation of a complex of the catalyst with polyunsaturated "red oil" isomerization by-product occurs and necessitates regeneration of the spent catalyst, preferably in a continuous catalyst regeneration zone. The spent catalyst can be regenerated by known methods such as by treatment of the resinous by-product complex with hydrogen at elevated temperatures and pressures, as disclosed in Hulme, U.S. Pat. No. 4,120,912, or by displacement of the metal pentafluoride from the resinous complex with a Lewis acid such as aluminum bromide, as disclosed in Hulme, U.S. Pat. No. 4,065,405. Another method of regenerating the catalyst is hydrolysis of the by-product complex with sufficient water to separate the "red oil" and subsequent dehydration of the hydrolyzed catalyst with molecular chlorine, as disclosed in Siskin, et al., U.S. Pat. No. 4,069,268.

One suitable and preferred continuous procedure for practicing the isomerization is illustrated in FIG. 1. In FIG. 1, after being hydrogenated and desulfurized (not shown), a suitable feed is introduced through line 11 into the reactor 12 with catalyst entering thereinto from line 13. Fresh metal pentafluoride is introduced through line 14 into a stream of hydrogen fluoride in the line 13. Hydrogen is introduced into the reactor 12 through line 15. The reaction mixture in the reactor 12 is maintained and stirred under conditions of total pressure, hydrogen partial pressure and WHSV in the aforedescribed ranges with the aforedescribed catalyst system and at a temperature in the range of $-60°$ C. to $-10°$ C. Under such conditions and in some cases after as little as 15 minutes, 2,6-dimethyldecalin originally present in the feed and being formed in the reaction mixture crystallizes out of solution. As it precipitates, additional 2,6-dimethyldecalin is formed by the isomerization reaction, and ultimately at least about 85 weight percent of the dicyclic naphthenes containing 12 carbon atoms in the reactor 12 is precipitated as 2,6-dimethyldecalin. At this point, the product stream is withdrawn through line 21 from the reactor 12 in the form of a slurry and circulated through either line 22 and valve 23 or line 24 and valve 25 to filter 31 or 32, respectively. Only one valve 23 or 25 is open at any given time. After one such filter 31 or 32 is filled with crystals, the open valve 23 or 25 is closed and the other valve is opened, to permit the slurry from the reactor 12 to flow through the other filter 31 or 32. Liquid catalyst passes through the filters 31 and 32 and is transmitted through lines 33 and 34 to line 35 through which most of the catalyst is recirculated to the reactor 12, except for a portion thereof withdrawn through line 36 for regeneration (not shown). Upon warming above its melting point (46° C.), the 2,6-dimethyldecalin crystals retained in the filters 31 and 32 liquefy and separate from occluded catalyst and are withdrawn and recovered through the lines 37 and 38.

Preparation of Mixtures of 2,6-Dimethyldecalin and Dicyclic Naphthenic Isomers Thereof In another respect, this invention involves a method for preparing a mixture of 2,6-dimethyldecalin and 12 carbon atom-containing dicyclic naphthenic isomers thereof, which mixtures can serve as suitable feeds for the aforesaid isomerization, by catalytically dimerizing methylcyclopentane or cyclohexane or both in the presence of a catalyst system comprising a liquid solution of tantalum pentafluoride or niobium pentafluoride in substantially anhydrous hydrogen fluoride. While not intending to be limited by any theory or explanation, I believe the dimerization probably proceeds through an initial rate-determining, ring-opening reaction to form a hexyl cation. The hexyl cation is believed to abstract a hydride ion from methylcyclopentane or cyclohexane. The resulting methylcyclopentyl cation or cyclohexyl cation undergoes an addition reaction with a methylcyclopentane or cyclohexane molecule, or with a methylcyclopentane or cyclohexene molecule in equilibrium with the cation, to form an equilibrium mixture of dicyclic naphthenes containing 12 carbon atoms, one of which is 2,6-dimethyldecalin.

When acyclic paraffins as well as methylcyclopentane and/or cyclohexane are present in the feed to this dimerization reaction, a reaction of methylcyclopentane and/or cyclohexane with acyclic paraffins which is competitive with the desired dimerization is alkylation of methylcyclopentane/cyclohexane. In order to favor the dimerization reaction over the alkylation reaction, it is essential to maintain the initial concentration of methylcyclopentane/cyclohexane in the dimerization reaction in the range of from about 40 weight percent, preferably from about 55 weight percent, to about 100 weight percent, preferably to about 85 weight percent, more preferably to about 80 weight percent. This can be effected by any convenient pre-concentration step or preferably, as will be described hereinbelow, by recycling a fraction containing a high concentration of unreacted methylcyclopentane/cyclohexane from the dimerization step back to the feed to the dimerization step.

As in the aforesaid isomerization method, sulfur-containing compounds, aromatics, and other unsaturated hydrocarbons form complexes with and hasten deactivation of the catalyst system. Consequently, unless its contents of sulfur-containing compounds and of aromatics and other unsaturated hydrocarbons are sufficiently low, preferably the feed to the method of this invention is hydrogenated and desulfurized or the unsaturated and sulfur-containing materials are otherwise removed from the feeds. Preferably the upper limits of the concentrations of sulfur-containing compounds, aromatic compounds and other unsaturated compounds in the feed are as described hereinabove for the aforesaid isomerization reaction. Typically, suitable feeds boil in the range of from about 30° C., preferably from about 35° C., to about 230° C.

While not essential to the dimerization reaction, the presence of preferably from about 15, more preferably from about 20, preferably to about 60, more preferably to about 45, weight percent of acyclic paraffins containing 5 to 12 carbon atoms and boiling in the range of from about 30° C., preferably from about 35° C., to about 230° C., with the dimethylcyclopentane or cyclohexane or both in the feed to the dimerization step of the method of this invention can have a significant beneficial effect on the dimerization reaction. Such acyclic paraffins undergo fission and accept hydrogen which is eliminated in the reaction forming the dicyclic naphthenes from methylcyclopentane or cyclohexane and thus surprisingly promote the dimerization.

For example, other things being equal and when performed in the absence of hydrogen, the presence of about 20 volume percent of hydrogenated light naphtha in the feed to the dimerization results in an approximately 5-fold increase in the initial rate of reaction of the methylcyclopentane/cyclohexane. However, under such conditions, catalyst activity decreases to about one-half its initial value in less than half the time than for the naphtha-free case. In the presence of 2.38 atmospheres of hydrogen and 44.5 volume percent of either light or heavy naphtha in the feed, the dimerization of methylcyclopentane/cyclohexane proceeds at an initial rate which is approxmately 10-fold greater and with about a 4-fold longer catatalyst life than the rate and catalyst life contained under the same conditions except for the absence of naphtha in the feed. However, the addition of the higher boiling n-hexadecane has little effect on the initial rate of the dimerization reaction or of the catalyst life. In addition to affecting the rate of the dimerization reaction and the useful life of the dimerization catalyst system, the components of the naphtha present in the feed are converted to more valuable high-octane number products, as generally disclosed in the aforesaid McCaulay et al, U.S. Pat. No. 4,214,116 and copending and allowed U.S. patent application Ser. No. 47,059, each of which in its entirety is specifically incorporated herein by reference.

Thus, feeds which are less expensive and more readily available than pure methylcyclopentane and/or cyclohexane are suitable and in fact are preferred in this dimerization step. For example, particularly suitable hydrocarbon fractions for the feed to the dimerization step of the preferred method of this invention include methylcyclopentane or cyclohexane or both and a hydrogenated, desulfurized naphtha fraction containing acyclic paraffins boiling from about 30° C. to about 230° C., such as hydrogenated gasoline or a portion thereof.

The presence of hydrogen also has a significant effect on the dimerization reaction. For example, when contacted with the catalyst described hereinbelow and in the absence of hydrogen, methcyclopentane and/or cyclohexane react to form hexanes and 12 carbon atom-containing dicyclic naphthenes, including dimethyldecalins, and after about 55 hours of reaction, the catalytic activity and reaction rate decline to about 50 percent of their initial values. However, other things being equal, when the reaction is performed in the presence of hydrogen in the range of partial pressures described hereinbelow, the initial catalyst activity is maintained and the reaction rate does not decrease over a similar 55-hour period of reaction. However, when performed under significantly higher partial pressures of hydrogen than the range described hereinbelow, the conversion of methylcyclopentane/cyclohexane to hexanes proceeds at a substantially constant rate over even a 12-fold longer reaction period, but the dimerization to the aforesaid dicyclic naphthenes is suppressed. Consequently, the partial pressure of hydrogen must be maintained in the range of from about 0.7 to about 20, preferably 7, atmospheres in order to effect dimerization of methylcyclopentane and/or cyclohexane to 12 carbon atom-containing dicyclic naphthenes. The total pressure under which the dimerization is performed must be high enough to maintain the reaction mixture and catalyst system substantially in the liquid state.

The catalyst system employed in the dimerization reaction comprises a liquid solution of a pentafluoride of tantalum or niobium in anhydrous liquid hydrogen fluoride. The dimerization catalyst system is defined as broadly and as having the same preferred forms and ratios as indicated hereinabove for the isomerization catalyst system.

The temperature at which the dimerization is performed is selected to permit dimerization to occur at a sufficiently rapid rate but not to facilitate the occurrence of undesirable side reactions and is suitably in the range of from about 10° C., preferably from about 25° C., to about 90° C., preferably to about 60° C.

The WHSV is a function of catalyst activity and is suitably in the range of from about 0.1, preferably from about 0.4, to about 7, preferably to about 5, grams of feed per gram of metal pentafluoride in the catalyst system per hour. Generally, operation at lower temperatures requires the use of correspondingly lower space velocities and at temperatures in the range of 15° C. to 30° C., the WHSV should be in the range of from about 0.4, preferably from about 0.5, to about 3.0, preferably to about 2.5 grams of feed per gram of metal pentafluoride in the catalyst system per hour.

As in the aforesaid isomerization, the presence of hydrogen in the dimerization reaction serves to inhibit the formation of "red oil." Nevertheless, the dimerization catalyst system does undergo gradual deactivation as a result of its complexation with "red oil" and can be regenerated as described hereinabove for the aforesaid isomerization reaction.

Figure 2:
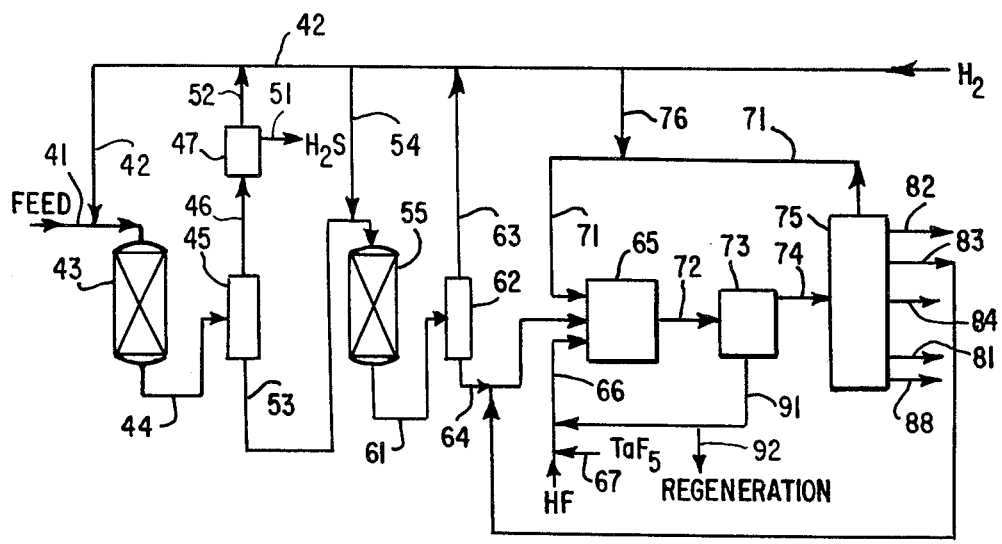
FIG. 2 is a schematic illustration of one preferred embodiment of the method of this invention in which the feed stream of FIG. 1 is generated by continuously and catalytically treating a hydrocarbon fraction comprising methylcyclopentane, cyclohexane and a naphtha fraction comprising acyclic paraffins and other monocyclic naphthenes and thereby dimerizing the methylcyclopentane and cyclohexane and hydrocracking and isomerizing the acyclic paraffins and monocyclic naphthenes and subsequently fractionating the resulting product stream.

Referring now to FIG. 2, which illustrates a preferred continuous procedure for performing the dimerization, a light naphtha fraction containing hydrocarbons having 6 to 7 carbon atoms and having an ASTM boiling range of from about 52° C. to about 93° C. is introduced through line 41 and admixed therein with hydrogen from line 42 and the resulting hydrogenated mixture is introduced into desulfurizer 43. In the desulfurizer 43, the sulfur content of the light naphtha fraction is reduced to about 1-3 parts per million by weight. The resulting mixture is then passed through the line 44 into the separator 45 where hydrogen sulfide and excess hydrogen are separated from the desulfurized naphtha. The gases are conducted from the separator 45 through line 46 to separator 47 where hydrogen sulfide is separated out through line 51 and the hydrogen is recycled through line 52 to the line 42. The desulfurized naphtha is conducted from the separator 45 through line 53. Hydrogen is introduced through line 54 into the naphtha in line 53 and the resulting mixture is introduced into a hydrogenation reactor 55 where the olefins and aromatics are saturated. It is of course possible, if desired, to combine desulfurization and saturation into one operation.

The saturated feed is then passed through line 61 to a separator 62 where excess hydrogen and the feed are separated, with the hydrogen being recycled to the line 42 through line 63. The feed is then passed through line 64 into dimerization reactor 65 where it is stirred under conditions of temperature, total pressure, hydrogen partial pressure and WHSV in the respective aforedescribed ranges with the aforedescribed dimerization step catalyst system introduced thereinto through line 66. Fresh metal pentafluoride is introduced through line 67 into a stream of hydrogen fluoride in line 66. Hydrogen is introduced into the dimerization reactor 65 through line 71.

The effluent from the reactor 65 passes through the line 72 to the settler 73 where the heavier catalyst phase separates as a lower layer and is withdrawn via line 91. Most of the withdrawn catalyst is then recycled to the reactor 65 through the line 66, except for a portion thereof withdrawn through line 92 for regeneration (not shown). The separated upper phase is then conducted through line 74 to a distillation zone 75 where it is fractionated. A fraction comprising at least 80, preferably at least 85, weight percent of dicyclic naphthenes and boiling in the range of from about 210° C., preferably from about 215° C., to about 230° C., preferably to about 225° C., is withdrawn from near the bottom of the column through line 81. This fraction serves as the feed to the aforesaid isomerization step of the method of this invention.

In addition, hydrogen and hydrogen fluoride are separated and recycled through line 71 to the reactor 65. Fresh hydrogen is added to the line 71 through line 76. A fraction containing paraffins containing 4 to 6 carbon atoms as well as methylcyclopentane and branched heptanes and boiling in the range of from about −15° C., preferably from about −12° C., to about 75° C., preferably to about 70° C., is separated and withdrawn through line 82. The portion of this fraction which contains at least 5 carbon atoms has a motor octane number of about 85 and can be used as a premium gasoline component. A fraction rich in cyclohexane and boiling in the range of from about 70° C., preferably from about 75° C., to about 90° C., preferably to about 85° C., is separated and recycled through lines 83 and 64 to the reactor 65. The ratio of recycle to fresh feed must be sufficiently high to maintain the combined concentration of methylcyclopentane/cyclohexane in the feed to the reactor 65 at the desired level. A fraction comprising mainly methylcyclohexane and polymethylcyclohexanes and boiling in the range of from about 100° C. to about 210° C. is separated and withdrawn through line 84. This fraction can be dehydrogenated (not shown) to form a mixture of toluene, xylenes and trimethylbenzene by any convenient and conventional method, such as by contact with a non-isomerizing catalyst such as alkalized chromia on alumina or platinum on silica by conventional methods well known in the art. The resulting xylenes and trimethylbenzenes are substantially free of ethylbenzene and ethyltoluene.

Pre-Concentration of 12-Carbon Atom-Containing Dicyclic Naphthenes

In another preferred embodiment of the isomerization method of this invention, a preferred feed for the isomerization can be obtained by contacting a hydrocarbon fraction containing a relatively small concentration of one or more dicyclic naphthenes having 12 carbon atoms with the aforesaid isomerization catalyst system. While some isomerization of 2,6-dimethyldecalin isomers to 2,6-dimethyldecalin does occur, the primary purpose of this catalytic pretreatment is to convert diluent materials boiling in the range of the dicyclic naphthenic isomers of 2,6-dimethyldecalin to materials which boil outside such range and thereby to effectively increase the concentration of such isomers within such boiling point range fraction.

As indicated above, sulfur-containing compounds, aromatic compounds, and other unsaturated hydrocarbons form complexes with and hasten deactivation of the isomerization catalyst system. Consequently, unless the concentrations of sulfur-containing compounds and of aromatics and other unsaturated organic compounds in the aforesaid hydrocarbon fraction are sufficiently low as not to substantially hasten the deactivation of the catalyst system, preferably the feed to the catalytic pretreatment method of this invention is hydrogenated and desulfurized, or the unsaturated and sulfur-containing compounds are otherwise removed from the feed. The preferred upper limits of the concentrations of sulfur-containing compounds, aromatic compounds, and other unsaturated compounds in the feed are as described hereinabove for the isomerization reaction.

Suitable hydrocarbon fractions for the feed to this catalytic pretreatment include those having a total concentration of dicyclic naphthenes of 12 carbon atoms of at least about 5 weight percent, preferably at least about 10 weight percent. Preferably such fractions have sufficiently low concentrations of sulfur-containing compounds and of aromatic and other unsaturated hydrocarbon compounds as not to deactivate the catalyst system, and suitably boil in the range of from about 180° C. to about 270° C. Thus, hydrocarbon fractions for the feed to this isomerization step of the method of this invention typically include a hydrogenated cut of light virgin gas oil or light catalytic cycle oil boiling in the aforedescribed ranges. Normally, such fractions include components, namely acyclic paraffins containing from 10 to 13 carbon atoms which cannot ordinarily be separated by distillation from the aforesaid dicyclic naphthenes of 12 carbon atoms. Consequently, such acyclic paraffins act as a diluent or solvent which can interfere with the crystallization of 2,6-dimethyldecalin or even with its formation. On the contrary, in this preferred embodiment of the method of this invention, the potentially interfering materials are hydrocracked and isomerized, forming materials which do not interfere with the formation of the dimethyldecalins and which can readily be separated on the basis of boiling point differences from the resulting dicyclic naphthenes of 12 carbon atoms. Furthermore, as an added benefit and as discussed hereinabove, in the hydrocracking operation, the acyclic paraffins and other monocyclic naphthenes in the feed are converted to more valuable high octane number products. For example, if large yields of gasoline and/or alkylbenzenes are desired, a naphtha fraction may also be included in the feed to the catalytic pretreatment. Thus, not only a preferred feed to the aforesaid isomerization but also additional upgraded hydrocarbon fractions are obtained by this catalytic pretreatment.

The broad and preferred ranges of weight ratio of the metal pentafluoride to hydrogen fluoride in the isomerization catalyst system as employed in this catalytic pretreatment are the same as defined for the isomerization. The broad and preferred ranges of WHSV and temperature employed in the catalytic pretreatment are the same as defined for the dimerization. The broad and preferred ranges of hydrogen partial pressure under which the catalytic pretreatment is performed are the same as defined for the isomerization. Even under such hydrogen partial pressures, the catalyst system does undergo gradual deactivation as a result of its complexation with "red oil" and can be regenerated as described hereinabove. The isomerization is performed at a sufficiently high total pressure in order to maintain the feed and catalyst system substantially in the liquid state.

Figure 3:
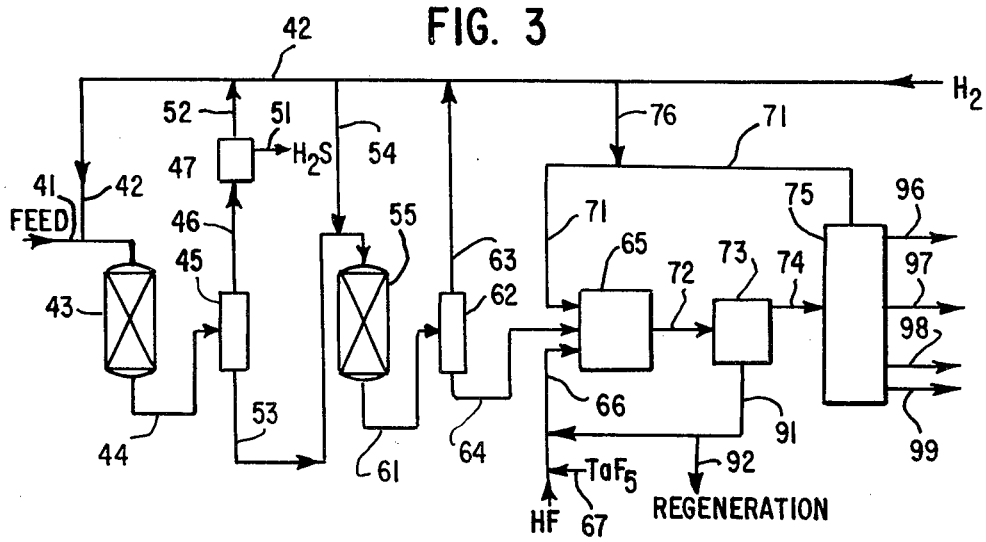
FIG. 3 is a schematic illustration of a second preferred embodiment of the method of this invention in which the feed stream of FIG. 1 is generated by continuously and catalytically treating a hydrocarbon fraction comprising 12 carbon atom-containing dicyclic naphthenes and a naphtha fraction comprising acyclic paraffins and monocyclic naphthenes and thereby isomerizing the dicyclic naphthenes and isomerizing and cracking the acyclic paraffins and monocyclic naphthenes and thereafter fractionating the resulting product stream.

Referring now to FIG. 3, all process units and transfer lines illustrated therein which have the same function as the corresponding units in FIG. 2 are numbered as in FIG. 2 and are not described further hereinafter. In FIG. 3, unlike in FIG. 2, a light catalytic cycle oil boiling between 180° C. and 275° C. is introduced through line 41. The light cycle oil is desulfurized in the desulfurizer 43, hydrogenated in the hydrogenation reactor 55, and contacted with a catalyst in the reactor 65. The resulting reaction product mixture is fractionated in the distillation zone 75. A fraction comprising primarily dicyclic naphthenes and boiling in the range of from about 210° C., preferably from about 215°0 C., to about 230° C., preferably to about 225° C., is withdrawn from near the bottom of the zone 75 through the line 98. This fraction serves as the feed to the aforesaid isomerization step of the method of this invention.

In addition, hydrogen and hydrogen fluoride are separated and recycled through line 71 to the reactor 65. A fraction containing paraffins containing 4 to 7 carbon atoms as well as methylcyclopentane, cyclohexane and branched heptanes and boiling between −15° C. and 100° C. is separated and withdrawn through line 96. The portion of this fraction which contains at least 5 carbon atoms has a motor octane number of about 85 and can be used as a premium gasoline component. A fraction comprising mainly methylcyclohexane and polymethylcyclohexanes and boiling between 100° C. and 210° C. is separated and withdrawn through line 97. This fraction can be dehydrogenated (not shown) to form a mixture of toluene, xylenes and trimethylbenzene by contact with a non-isomerizing catalyst such as alkalized chromia on alumina or platinum on silica. The resulting xylenes and trimethylbenzenes are relatively free of ethylbenzene and ethyltoluene. A bottoms fraction heavier than the fraction withdrawn through the line 98 and boiling above 230° C. is withdrawn through line 99 and a portion thereof, if desired, can be recycled (not shown) to the reactor 65.

Each of the aforedescribed steps of this invention can be performed batchwise or continuously and preferably is performed continuously.

The present invention will be more clearly understood from the following specific examples. Examples 1–5 illustrate the deactivation of the dimerization catalyst system when used in the absence of hydrogen and the isomerization, ring opening and dimerization reactions of methylcyclopentane and/or cyclohexane in the presence of the dimerization catalyst system. Examples 6–14 illustrate that methylcyclopentane and/or cyclohexane do not dimerize in the presence of the dimerization catalyst system at high hydrogen partial pressures. Examples 15–28 illustrate the beneficial effects of hydrogen and light naphtha on the activity of the dimerization catalyst system and the products from the hydrocracking of the light naphtha. Similarly Examples 29–39 illustrate the beneficial effects of hydrogen and heavy naphtha on the activity of the dimerization catalyst system and the products from the hydrocracking of the heavy naphtha. Examples 40–44 illustrate the beneficial effects of naphtha on the activity of the dimerization catalyst system. Examples 45–47 illustrate that n-hexadecane has little effect on the dimerization catalyst system activity. Example 48 illustrates the isomerization of other dimethyldecalin isomers to 2,6-dimethyldecalin and the crystallization of 2,6-dimethyldecalin. Example 49 illustrates the dehydrogenation of monocyclic and dicyclic naphthenes. Example 50 illustrates the pre-concentration of the dicyclic naphthenes in a heavy naphtha followed by isomerization of the fraction thereof comprising 12 carbon atom-containing dicyclic naphthenes to form 2,6-dimethyldecalin which then crystallizes.

EXAMPLES 1–39

A single batch of catalyst, tantalum pentafluoride dissolved in liquid anhydrous hydrogen fluoride, was contacted in a closed stirred autoclave with successive batches of hydrocarbon feed. The reactor had a 300-milliliter capacity and was constructed of an inert material such as Hastelloy C or stainless steel. Reactor temperature was maintained by immersing the reactor in a glycol bath and by circulating a refrigerated glycol solution through a coil wrapped around the outside of the reactor and immersed in the glycol bath. Solid tantalum pentafluoride was first weighed into the open reactor, and kept dry by a sweep of dry nitrogen. The reactor was then closed and evacuated, and a measured amount of liquid anhydrous hydrogen fluoride was added thereto by displacement from a volume-measuring tube. The mixture was stirred, and hydrogen gas was introduced into the reactor until the desired partial pressure of hydrogen was reached. The hydrocarbon feed was added batchwise from a displacement pump. Stirring was stopped at intervals, and after settling, the hydrocarbon and catalyst settled into separate phases, and either an aliquot of the hydrocarbon layer or the entire remaining hydrocarbon layer was withdrawn through a standpipe terminating just above the acid-hydrocarbon interface. Then stirring was resumed. When the entire hydrocarbon layer was withdrawn, a new charge of feed was added before stirring was resumed. Samples of the hydrocabon products were analyzed by gas chromatography. The experimental parameters and results for Examples 1–5, 6–14, 15–28, and 29–39 are indicated in Tables I, II, III, and IV, respectively. The contact time in Tables I, II, III, and IV is the time during which the particular hydrocarbon (aliquot or entire remaining layer) withdrawn had been stirred with the catalyst, while the catalyst age is the total stirring and settling time during which the particular batch of catalyst had been in contact with hydrocarbon material (not just the particular aliquot or hydrocarbon layer withdrawn).

TABLE I

| Example No. | 1 | 2 | 3 | 4 | 5 |
|---|---|---|---|---|---|
| Conditions | | | | | |
| Sample Weight (g.) | 102 | 156.5 | 138 | 132 | 133.4 |
| Contact Time (hrs.) | 66.6 | 21.8 | 23.6 | 23.7 | 263.4 |
| Catalyst Age (hrs.) | 66.6 | 88.6 | 112.4 | 136.3 | 400 |
| Results | | | | | |
| Composition of Product (Weight Percent) | | | | | |
| propane | 0.1 | 0.0 | 0.0 | 0.0 | 0.0 |
| isobutane | 3.0 | 1.0 | 0.2 | 0.1 | 1.5 |
| isopentane | 0.3 | 0.1 | 0.0 | 0.0 | 0.0 |
| hexanes | 10.0 | 3.7 | 2.2 | 1.4 | 5.5 |
| methylcyclopentane | 7.4 | 10.9 | 11.3 | 8.8 | 6.2 |
| cyclohexane | 48.4 | 72.3 | 80.1 | 85.9 | 62.9 |
| methylcyclohexane | 1.5 | 0.2 | 0.0 | 0.0 | 0.3 |
| $C_8$ cyclohexanes | 5.8 | 1.8 | 0.4 | 0.1 | 3.4 |
| $C_9$ cyclohexanes | 1.2 | 0.3 | 0.0 | 0.0 | 0.3 |
| $C_{10}$ cyclohexanes | 0.3 | 0.1 | 0.0 | 0.0 | 0.2 |
| $C_{11}$ cyclohexanes | 0.3 | 0.0 | 0.0 | 0.0 | 0.0 |
| dimethyldecalins | 18.0 | 8.3 | 5.6 | 3.6 | 17.8 |
| higher | 3.7 | 1.3 | 0.2 | 0.1 | 1.9 |
| Composition of Hexane Product Fraction (Weight Percent) | | | | | |
| 2,2-dimethylbutane | 53.8 | 58.6 | 51.1 | 57.0 | 56.5 |
| 2,3-dimethylbutane | 8.9 | 8.7 | 8.1 | 30.3 | 29.9 |
| 2-methylpentane | 21.0 | 21.5 | 20.6 | | |
| 3-methylpentane | 12.9 | 9.8 | 17.9 | 9.9 | 9.8 |
| n-hexane | 3.4 | 1.4 | 2.2 | 2.8 | 3.8 |
| Rate A | .026 | .025 | .011 | .007 | .004 |
| Rate B | .0081 | .0113 | .0071 | .0045 | .002 |
| Rate C | .0045 | .0051 | .0028 | .0018 | .006 |

TABLE II

| Example No. | 6 | 7 | 8 | 9 | 10 |
|---|---|---|---|---|---|
| Conditions | | | | | |
| Sample Weight (g.) | 110.5 | 6.9 | 7.0 | 5.0 | 5.0 |
| Contact Time (hrs.) | 16.0 | 24.6 | 47.3 | 74.7 | 142.8 |
| Catalyst Age (hrs.) | 16.0 | 41.8 | 64.8 | 92.3 | 160.4 |
| Results | | | | | |
| Composition of Product (Weight Percent) | | | | | |
| propane | 0.0 | 0.0 | 0.0 | 0.0 | 0.0 |
| isobutane | 0.0 | 0.0 | 0.0 | 0.0 | 0.0 |
| n-butane | 0.0 | 0.0 | 0.0 | 0.0 | 0.0 |
| isopentane | 0.0 | 0.0 | 0.0 | 0.0 | 0.1 |
| hexanes | 4.4 | 8.8 | 12.5 | 19.9 | 32.2 |
| methylcyclopentane | 7.4 | 9.0 | 7.7 | 7.5 | 6.7 |

TABLE II-continued

| | | | | | |
|---|---|---|---|---|---|
| cyclohexane | 88.8 | 82.1 | 79.7 | 72.5 | 60.8 |
| methylcyclohexane | 0.0 | 0.0 | 0.0 | 0.0 | 0.0 |
| $C_8$ cyclohexanes | 0.0 | 0.0 | 0.0 | 0.0 | 0.0 |
| $C_9$ cyclohexanes | 0.0 | 0.0 | 0.0 | 0.0 | 0.0 |
| $C_{10}$ cyclohexanes | 0.0 | 0.0 | 0.0 | 0.0 | 0.0 |
| $C_{11}$ cyclohexanes | 0.0 | 0.0 | 0.0 | 0.0 | 0.0 |
| dimethyldecalins | 0.0 | 0.1 | 0.1 | 0.1 | 0.2 |
| higher | 0.0 | 0.0 | 0.0 | 0.0 | 0.0 |
| Composition of Hexane Product Fraction (Weight Percent) | | | | | |
| 2,2-dimethylbutane | 35.7 | 47.0 | 48.0 | 50.0 | 49.7 |
| 2,3-dimethylbutane | 44.2 | 35.8 | 35.0 | 33.7 | 33.8 |
| 2-methylpentane | — | — | — | — | — |
| 3-methylpentane | 16.3 | 12.3 | 12.0 | 11.4 | 11.6 |
| n-hexane | 3.8 | 4.9 | 5.0 | 4.9 | 4.9 |
| Rate A | .0098 | .0133 | .0100 | .011 | .0098 |

| Example No. | 11 | 12 | 13 | 14 |
|---|---|---|---|---|
| Conditions | | | | |
| Sample Weight (g.) | 4.5 | 3.5 | 9.9 | 80.0 |
| Contact Time (hrs.) | 314.1 | 481.1 | 646.1 | 669.6 |
| Catalyst Age (hrs.) | 331.8 | 498.9 | 664.2 | 688.2 |
| Results | | | | |
| Composition of Product (Weight Percent) | | | | |
| propane | 0.0 | 0.0 | 0.2 | 0.2 |
| isobutane | 0.1 | 0.1 | 0.1 | 0.1 |
| n-butane | 0.1 | 0.0 | 0.1 | 0.2 |
| isopentane | 0.2 | 0.2 | 0.4 | 0.7 |
| hexanes | 58.1 | 72.2 | 81.6 | 83.2 |
| methylcyclopentane | 4.4 | 3.0 | 2.0 | 1.5 |
| cyclohexane | 36.9 | 24.2 | 15.5 | 18.9 |
| methylcyclohexane | 0.0 | 0.0 | 0.0 | 0.0 |
| $C_8$ cyclohexanes | 0.1 | 0.1 | 0.1 | 0.1 |
| $C_9$ cyclohexanes | 0.0 | 0.0 | 0.0 | 0.0 |
| $C_{10}$ cyclohexanes | 0.0 | 0.0 | 0.0 | 0.0 |
| $C_{11}$ cyclohexanes | 0.0 | 0.0 | 0.0 | 0.0 |
| dimethyldecalins | 0.2 | 0.2 | 0.1 | 0.1 |
| higher | 0.0 | 0.0 | 0.0 | 0.0 |
| Composition of Hexane Product Fraction (Weight Percent) | | | | |
| 2,2-dimethylbutane | 52.4 | 52.9 | 52.8 | 53.2 |
| 2,3-dimethylbutane | 9.1 | 8.9 | 9.2 | 31.9 |
| 2-methylpentane | 23.2 | 23.2 | 23.2 | — |
| 3-methylpentane | 10.6 | 11.0 | 10.7 | 10.6 |
| n-hexane | 4.7 | 4.0 | 4.1 | 4.3 |
| Rate A | .0098 | .0098 | .0098 | .0099 |

TABLE III

| Example No. | 15 | 16 | 17 | 18 |
|---|---|---|---|---|
| Conditions | | | | |
| Sample Weight (g.) | 1.8 | 108 | 5.2 | 116 |
| Contact Time (hrs.) | 4.7 | 24.2 | 4.1 | 23.3 |
| Catalyst Age (hrs.) | 4.7 | 24.4 | 28.7 | 48.0 |
| Results | | | | |
| Composition (Weight Percent) | | | | |

| | Feed | Product | | | |
|---|---|---|---|---|---|
| propane | — | 1.7 | 3.5 | 1.7 | 3.2 |
| isobutane | — | 5.8 | 10.7 | 6.2 | 8.7 |
| n-butane | — | 0.2 | 0.3 | 0.2 | 0.3 |
| isopentane | 0.4 | 2.2 | 2.4 | 2.3 | 2.2 |
| n-pentane and cyclopentane | 1.3 | 0.7 | 0.7 | 0.5 | 0.7 |
| hexanes | 22.0 | 22.2 | 20.5 | 21.6 | 20.1 |
| methylcyclopentane | 55.5 | 5.2 | 4.0 | 5.3 | 4.0 |
| cyclohexane | 0.7 | 40.2 | 30.5 | 39.9 | 34.4 |
| $C_7$ branched paraffins | 10.4 | 2.7 | 0.4 | 4.8 | 1.4 |
| n-heptane | 3.2 ⎱ | 1.4 ⎱ | .03 ⎱ | 1.3 ⎱ | 2.0 ⎱ |
| methylcyclohexane | 0.2 | | 2.6 | | |
| $C_8$ branched paraffins | | 0.0 | 0.0 | 0.0 | 0.0 |
| $C_8$ cyclohexanes | 5.3 | 2.2 | 4.1 | 2.3 | 2.9 |
| n-octane | | 0.0 | 0.0 | 0.0 | 0.0 |
| $C_9$ paraffins | 0.9 | 0.0 | 0.0 | 0.0 | 0.0 |
| $C_9$ cyclohexanes | | 3.0 | 3.0 | 2.6 | 3.3 |
| $C_{10}$ cyclohexanes | 0.1 | 4.8 | 4.3 | 4.2 | 5.1 |
| decalin and methyldecalin | | 0.1 | 0.3 | 0.1 | 0.1 |
| dimethyldecalins | | 7.6 | 12.7 | 6.9 | 11.5 |
| higher | | 0.0 | 0.0 | 0.0 | 0.0 |
| Composition of Hexane Fraction (Weight Percent) | | | | | |

| | Feed | Product | | | |
|---|---|---|---|---|---|
| 2,2-dimethylbutane | 4.0 | 59.6 | 60.4 | 55.4 | 61.0 |
| 2,3-dimethylbutane / 2-methylpentane | 34.1 | 27.8 | 27.1 | 30.3 | 27.0 |
| 3-methylpentane | 26.5 | 8.8 | 8.7 | 9.6 | 8.5 |
| n-hexane | 35.4 | 3.8 | 3.8 | 4.7 | 3.5 |
| Rate A | | 0.25 | — | 0.29 | — |
| Rate B | | .072 | .022 | .074 | .022 |

| Example No. | 19 | 20 | 21 | 22 | 23 |
|---|---|---|---|---|---|
| Conditions | | | | | |
| Sample Weight (g.) | 5.8 | 117 | 6.1 | 115 | 9.6 |
| Contact Time (hrs.) | 4.9 | 95.4 | 4.2 | 23.4 | 4.7 |
| Catalyst Age (hrs.) | 53.3 | 143.9 | 148.1 | 167.9 | 172.8 |
| Results | | | | | |
| Composition (Weight Percent) | | | | | |

| | Product | | | | |
|---|---|---|---|---|---|
| propane | 1.4 | 3.3 | 0.9 | 1.8 | 0.8 |
| isobutane | 5.0 | 9.1 | 4.0 | 5.9 | 3.9 |
| n-butane | 0.2 | 0.3 | 0.1 | 0.2 | 0.1 |
| isopentane | 2.1 | 2.2 | 1.9 | 2.1 | 2.0 |
| n-pentane and cyclopentane | 0.7 | 0.6 | 0.8 | 0.7 | 0.9 |
| hexanes | 20.4 | 19.2 | 20.4 | 20.6 | 21.3 |
| methylcyclopentane | 5.5 | 3.8 | 5.7 | 6.3 | 6.2 |
| cyclohexane | 42.2 | 33.1 | 42.5 | 38.8 | 41.9 |
| $C_7$ branched paraffins | 5.9 | 1.1 | 7.0 | 4.7 | 8.2 |
| n-heptane | 1.8 | 2.2 | 1.6 | 0.8 | 0.8 |
| methylcyclohexane | 1.2 | 0.9 | 1.1 | 1.9 | |
| $C_8$ branched paraffins | 0.0 | 0.0 | 0.0 | 0.0 | 0.0 |
| $C_8$ cyclohexanes | 2.3 | 3.5 | 2.4 | 2.0 | 2.5 |
| n-octane | 0.0 | 0.0 | 0.0 | 0.0 | 0.0 |
| $C_9$ paraffins | 0.0 | 0.0 | 0.0 | 0.0 | 0.0 |
| $C_9$ cyclohexanes | 2.2 | 3.7 | 1.7 | 2.4 | 1.6 |
| $C_{10}$ cyclohexanes | 3.4 | 5.6 | 2.9 | 4.1 | 2.5 |
| decalin and methyldecalin | 0.1 | 0.3 | 0.3 | 0.2 | 0.1 |
| dimethyldecalins | 5.9 | 12.2 | 6.8 | 8.4 | 5.3 |
| higher | 0.0 | 0.0 | 0.0 | 0.0 | 0.0 |
| Composition of Hexane Fraction (Weight Percent) | | | | | |

| | Product | | | | |
|---|---|---|---|---|---|
| 2,2-dimethylbutane | 49.0 | 60.6 | 36.3 | 56.8 | 31.6 |
| 2,3-dimethylbutane / 2-methylpentane | 33.6 | 27.2 | 39.4 | 29.0 | 41.4 |
| 3-methylpentane | 10.8 | 8.6 | 12.8 | 9.4 | 13.6 |
| n-hexane | 6.6 | 3.6 | 11.5 | 4.9 | 13.3 |
| Rate A | 0.19 | — | 0.21 | — | 0.19 |
| Rate B | .053 | .006 | .071 | .016 | .050 |

| Example No. | 24 | 25 | 26 | 27 | 28 |
|---|---|---|---|---|---|
| Conditions | | | | | |
| Sample Weight (g.) | 110 | 12.5 | 106 | 8.8 | 111 |
| Contact Time (hrs.) | 23.4 | 4.8 | 23.6 | 4.4 | 22.7 |
| Catalyst Age (hrs.) | 191.9 | 197.1 | 216.0 | 221.4 | 239.8 |
| Results | | | | | |

TABLE III-continued

Composition (Weight Percent)

| | Product | | | | |
|---|---|---|---|---|---|
| propane | 1.4 | 0.6 | 0.4 | 0.4 | 0.8 |
| isobutane | 5.3 | 3.5 | 3.3 | 2.7 | 4.3 |
| n-butane | 0.2 | 0.1 | 0.2 | 0.1 | 0.2 |
| isopentane | 2.2 | 1.8 | 2.0 | 1.6 | 2.1 |
| n-pentane and cyclopentane | 0.7 | 0.9 | 0.4 | 1.0 | 0.7 |
| hexanes | 20.8 | 20.7 | 19.9 | 24.1 | 21.0 |
| methylcyclopentane | 6.0 | 6.0 | 6.1 | 5.3 | 5.9 |
| cyclohexane | 41.2 | 45.9 | 44.8 | 45.8 | 44.9 |
| C₇ branched paraffins | 5.9 | 8.2 | 7.0 | 7.0 | 7.4 |
| n-heptane | 1.0 | 2.0 | 1.7 | 1.5 | 1.3 |
| methylcyclohexane | 1.1 | 0.7 | 0.9 | 0.5 | 0.8 |
| C₈ branched paraffins | 0.0 | 0.0 | 0.0 | 0.0 | 0.0 |
| C₈ cyclohexanes | 2.2 | 2.4 | 2.1 | 1.6 | 2.1 |
| n-octane | 0.0 | 0.0 | 0.0 | 0.0 | 0.0 |
| C₉ paraffins | 0.0 | 0.0 | 0.0 | 0.0 | 0.0 |
| C₉ cyclohexanes | 2.2 | 1.2 | 2.0 | 1.1 | 1.7 |
| C₁₀ cyclohexanes | 3.4 | 1.8 | 2.9 | 1.2 | 2.0 |
| decalin and methyldecalin | 0.1 | 0.1 | 0.0 | 0.1 | 0.0 |
| dimethyldecalins | 6.5 | 4.0 | 5.9 | 6.2 | 4.9 |
| higher | 0.0 | 0.0 | 0.0 | 0.0 | 0.0 |

Composition of Hexane Fraction (Weight Percent)

| | Product | | | | |
|---|---|---|---|---|---|
| 2,2-dimethylbutane | 53.0 | 27.3 | 43.1 | 34.2 | 41.4 |
| 2,3-dimethylbutane / 2-methylpentane | 31.5 | 43.2 | 37.0 | 37.9 | 37.5 |
| 3-methylpentane | 10.1 | 14.1 | 12.4 | 12.5 | 12.2 |
| n-hexane | 5.4 | 15.4 | 7.5 | 1.54 | 8.9 |
| Rate A | — | 0.12 | — | 0.14 | — |
| Rate B | .012 | .037 | .011 | .062 | .009 |

TABLE IV

| Example No. | 29 | 30 | 31 | 32 |
|---|---|---|---|---|
| Conditions | | | | |
| Sample Weight (g.) | 103 | 5.0 | 114 | 7.6 |
| Contact Time (hrs.) | 19.7 | 7.0 | 23.2 | 7.3 |
| Catalyst Age (hrs.) | 19.7 | 27.3 | 43.7 | 51.3 |
| Results | | | | |

Composition Product (Weight Percent)

| | Feed | Product | | | |
|---|---|---|---|---|---|
| propane | — | 0.7 | 0.4 | 0.4 | 0.2 |
| isobutane | — | 11.1 | 6.7 | 7.0 | 5.3 |
| n-butane | — | 0.4 | 0.3 | 0.5 | 0.2 |
| isopentane | — | 3.2 | 3.2 | 3.5 | 2.9 |
| n-pentane | — | 0.6 | 0.6 | 0.8 | 0.4 |
| hexanes | 0.4 | 3.1 | 2.5 | 3.4 | 2.2 |
| methylcyclopentane | 52.4 | 4.3 | 4.5 | 4.5 | 4.6 |
| cyclohexane | 0.5 | 30.7 | 36.7 | 35.8 | 37.9 |
| C₇ branched paraffins | 1.4 | 0.2 | 1.2 | 0.9 | 1.4 |
| n-heptane | 2.6 | 0.0 | 0.4 | 0.3 | 0.5 |
| dimethylcyclopentanes | 3.2 | 0.0 | 0.0 | 0.0 | 0.0 |
| methylcyclohexane | | 6.0 | 4.5 | 5.1 | 4.6 |
| C₈ paraffins | 6.6 | 0.0 | 0.8 | 0.5 | 1.3 |
| C₈ cyclohexanes | 5.9 | 7.4 | 6.6 | 6.4 | 7.6 |
| C₈ cyclopentanes | 0.0 | 0.0 | 0.0 | 0.0 | 0.0 |
| C₉ paraffins | 6.6 | 0.0 | 1.3 | 1.1 | 1.8 |
| C₉ naphthenes | 7.0 | 8.7 | 7.5 | 8.2 | 8.9 |
| C₁₀ paraffins | 6.3 | 0.0 | 0.7 | 0.0 | 1.8 |
| C₁₀ naphthenes | 6.0 | 6.4 | 7.9 | 7.8 | 7.5 |
| C₁₁ paraffins | 0.4 | 0.0 | 0.1 | 0.0 | 0.2 |
| higher | 0.7 | — | — | — | — |
| Decalin and methyldecalin | | 2.0 | 1.0 | 0.7 | 0.7 |
| Dimethyldecalins | | 15.4 | 12.1 | 12.8 | 10.0 |

Composition of Hexane Fraction (Weight Percent)

| | Feed | Product | | | |
|---|---|---|---|---|---|
| 2,2-dimethylbutane | 1.8 | 58.7 | 49.8 | 55.7 | 37.1 |
| 2,3-dimethylbutane / 2-methylpentane | 11.9 | 29.2 | 33.4 | 29.4 | 41.8 |
| 3-methylpentane | 6.7 | 9.0 | 12.0 | 10.5 | 14.2 |
| n-hexane | 79.5 | 2.9 | 4.8 | 4.4 | 6.9 |
| Rate A | — | — | 0.23 | — | 0.20 |
| Rate B | — | .034 | .076 | — | .060 |

| Example No. | 33 | 34 | 35 | 36 | 37 |
|---|---|---|---|---|---|
| Conditions | | | | | |
| Sample Weight (g.) | 124 | 4.9 | 121 | 17.3 | 116 |
| Contact Time (hrs.) | 23.5 | 7.0 | 23.4 | 7.3 | 61.5 |
| Catalyst Age (hrs.) | 67.6 | 75.2 | 91.8 | 99.6 | 163.9 |
| Results | | | | | |

Composition (Weight Percent)

| | Product | | | | |
|---|---|---|---|---|---|
| propane | 0.4 | 0.1 | 0.3 | 0.1 | 0.3 |
| isobutane | 6.6 | 4.2 | 5.7 | 3.9 | 6.0 |
| n-butane | 0.3 | 0.2 | 0.2 | 0.2 | 0.2 |
| isopentane | 3.3 | 2.7 | 3.0 | 2.5 | 3.1 |
| n-pentane | 0.5 | 0.3 | 0.5 | 0.2 | 0.5 |
| hexanes | 2.4 | 2.1 | 2.2 | 1.9 | 2.2 |
| methylcyclopentane | 5.2 | 4.9 | 5.1 | 5.9 | 5.5 |
| cyclohexane | 36.8 | 40.7 | 37.9 | 41.8 | 36.8 |
| C₇ branched paraffins | 1.2 | 1.5 | 1.4 | 1.5 | 1.4 |
| n-heptane | 0.5 | 1.0 | 0.7 | 1.3 | 0.5 |
| dimethylcyclopentanes | 0.0 | 0.0 | 0.0 | 0.0 | 0.0 |
| methylcyclohexane | 4.2 | 4.1 | 3.7 | 4.0 | 3.9 |
| C₈ paraffins | 1.1 | 2.6 | 1.5 | 3.4 | 1.3 |
| C₈ cyclohexanes | 6.2 | 6.8 | 6.3 | 6.7 | 6.2 |
| C₈ cyclopentanes | 0.0 | 0.0 | 0.0 | 0.0 | 0.0 |
| C₉ paraffins | 1.7 | 2.8 | 1.9 | 3.4 | 1.7 |
| C₉ naphthenes | 8.0 | 7.8 | 7.8 | 7.3 | 7.9 |
| C₁₀ paraffins | 0.7 | 1.8 | 1.5 | 2.0 | 1.4 |
| C₁₀ naphthenes | 7.8 | 6.7 | 7.0 | 6.5 | 7.0 |
| C₁₁ paraffins | 0.1 | 0.2 | 0.2 | 0.3 | 0.2 |
| higher | — | — | — | — | — |
| Decalin and methyldecalin | 0.9 | 0.6 | 1.0 | 0.6 | 0.9 |
| Dimethyldecalins | 12.3 | 8.9 | 12.2 | 7.7 | 13.0 |

Composition of Hexane Fraction (Weight Percent)

| | Product | | | | |
|---|---|---|---|---|---|
| 2,2-dimethylbutane | 50.0 | 25.9 | 40.2 | 17.5 | 43.5 |
| 2,3-dimethylbutane / 2-methylpentane | 34.1 | 48.3 | 40.2 | 51.9 | 37.7 |
| 3-methylpentane | 11.3 | 17.1 | 13.7 | 19.6 | 13.0 |
| n-hexane | 4.6 | 8.8 | 5.9 | 11.1 | 5.8 |
| Rate A | — | 0.16 | — | 0.13 | — |
| Rate B | .033 | .056 | .033 | .046 | .009 |

| Example No. | 38 | 39 |
|---|---|---|
| Conditions | | |
| Sample Weight (g.) | 6.6 | 116 |
| Contact Time (hrs.) | 7.3 | 23.4 |
| Catalyst Age (hrs.) | 171.5 | 187.7 |
| Results | | |

Composition (Weight Percent)

| | Product | |
|---|---|---|
| propane | 0.1 | 0.1 |
| isobutane | 3.2 | 4.3 |
| n-butane | 0.1 | 0.2 |
| isopentane | 2.2 | 2.7 |
| n-pentane | 0.2 | 0.3 |
| hexanes | 1.7 | 2.0 |
| methylcyclopentane | 4.9 | 5.1 |
| cyclohexane | 42.5 | 40.4 |

TABLE IV-continued

| | | |
|---|---|---|
| C7 branched paraffins | 1.4 | 1.6 |
| n-heptane | 1.3 | 1.1 |
| dimethylcyclopentanes | 0.0 | 0.0 |
| methylcyclohexane | 3.8 | 3.9 |
| C8 paraffins | 3.5 | 2.5 |
| C8 cyclohexanes | 7.5 | 7.0 |
| C8 cyclopentanes | 0.0 | 0.0 |
| C9 paraffins | 3.3 | 2.7 |
| C9 naphthenes | 7.7 | 7.7 |
| C10 paraffins | 2.1 | 2.3 |
| C10 naphthenes | 6.4 | 6.3 |
| C11 paraffins | 0.3 | 0.2 |
| higher | — | — |
| Decalin and methyldecalin | 0.4 | 0.6 |
| Dimethyldecalins | 7.4 | 9.1 |

Composition of Hexane Fraction (Weight Percent)

| | Product | |
|---|---|---|
| 2,2-dimethylbutane | 12.5 | 21.0 |
| 2,3-dimethylbutane / 2-methylpentane | 54.8 | 51.4 |
| 3-methylpentane | 20.6 | 18.1 |
| n-hexane | 13.1 | 9.5 |
| Rate A | 0.13 | — |
| Rate B | .045 | .025 |

In Tables I, II, III, and IV, Rate A is the rate of reaction of methylcyclopentane and/or cyclohexane, Rate B is the rate of formation of dimethyldecalins and rate C is the rate of formation of hexanes. Rates A, B, and C each are expressed in units of grams of methylcyclopentane/cyclohexane reacted, dimethyldecalins formed or hexanes formed, respectively, per hour per gram of tantalum pentafluoride.

Examples 1-5 involve contacting consecutive batches of 132 grams of a hydrocarbon feed of methylcyclopentane, contacted with a single batch of a catalyst comprising 44.3 grams of tantalum pentafluoride dissolved in 40 grams of anhydrous hydrogen fluoride, in a Hastelloy C reactor and at 25° C., a total pressure of one atmosphere, and no hydrogen partial pressure. The results in Table I for Examples 1-5 illustrate that methylcyclopentane isomerizes to cyclohexane and also undergoes a ring-opening reaction forming n-hexyl cations which can then isomerize to form other hexyl isomers. In addition, other secondary products are formed from the breakdown of dimethyldecalins formed during the reaction. Furthermore, the variations in rate A, B, and C in Examples 1-5 illustrate that the catalyst system gradually loses its activity with time on stream. Examination of the catalyst at the end of the run revealed that it contained about 10 weight percent of "red oil," a $C_{15}-C_{30}$ polyolefinic hydrocarbon similar to the contaminant that accumulates in alkylation and other acid-catalyzed processes. The "red oil" is a base in a strong acid environment and is responsible for the loss of acidity. A semilog plot (not shown) of Rate A versus time on stream for Examples 1-5 illustrates that the half life (time for loss of half of the initial catalytic activity) of the catalyst is about 55 hours when neither hydrogen nor acyclic paraffins are present in the hydrocarbon feed.

Examples 6-14 involve contacting batches of a hydrocarbon feed of methylcyclopentane with a catalyst comprising 37.7 grams of tantalum pentafluoride dissolved in 40 grams of anhydrous hydrogen fluoride in a Hastelloy C reactor and at 25° C., at a total pressure of 41.8 atmospheres and a hydrogen partial pressure of 40.8 atmospheres. New charges of 132 grams of the feed were introduced into the reactor in Examples 6 and 7. The entire remaining hydrocarbon layers were withdrawn in Examples 6 and 14, and aliquots of the hydrocarbon layer were withdrawn in Examples 7-13.

The Rates A in Examples 6-14 illustrate that in the presence of hydrogen at a partial pressure of 40.8 atmospheres, the initial reaction rate of methylcyclopentane/cyclohexane is approximately the same as in Examples 1-5 where no hydrogen is present but that the catalyst retains substantially all of its activity at least after almost 700 hours on stream. However, in Examples 6-14 only a small steady state concentration of dimethyldecalins result, indicating that essentially only the ring-opening and isomerization reactions occur at high hydrogen partial pressures.

Examples 15-28 involve contacting batches of a hydrocarbon feed comprising 55.5 volume percent of methylcyclopentane and 44.5 volume percent of a light naphtha, with a single batch of catalyst comprising 30 grams of tantalum pentafluoride dissolved in 60 grams of hydrogen fluoride, in a stainless steel reactor at 25° C., at a hydrogen partial pressure of 2.04 atmospheres and under a total pressure of 3.04 atmospheres. The composition of the feed is given in Table III. The light naphtha employed was the gasoline fraction of reformate which had been produced by reforming a desulfurized feedstock, and from which the aromatics had thereafter first been removed by extraction and then by treatment with fuming sulfuric acid. New charges of 132 grams of the feed were introduced into the reactor in Examples 15, 17, 19, 21, 23, 25, and 27. Aliquots of the hydrocarbon layers were withdrawn in each of Examples 15, 17, 19, 21, 23, 25, and 27 and the entire remaining hydrocarbon layers were withdrawn in Examples 16, 18, 20, 22, 24, 26, and 28.

The results in Table III for Examples 15-28 indicate that under a hydrogen partial pressure of 2.04 atmospheres and with a hydrocarbon feed comprising methylcyclopentane and light naphtha, the rates of conversion of methylcyclopentane/cyclohexane indicate that the initial catalyst activity is about 10-fold greater than when the reaction is performed in the absence of the light naphtha and hydrogen but otherwise under the same conditions. Comparison with the results in Table V hereinbelow for Examples 43-47 indicates that the presence of hydrogen slows the rate of loss of catalytic activity and affords a 4-fold increase in useful catalyst life.

The results in Table III further indicates that about half of the recited methylcyclopentane/cyclohexane forms dimethyldecalins and the other half thereof forms alkylated cyclohexanes containing from 7 to 10 carbon atoms. Although their total concentrations remain substantially unchanged by the reaction, the pentanes and hexanes are each isomerized to more closely approximate an equilibrium mixture of their isomers.

While not intending to be bound by a theoretical explanation or interpretation of the experimental results, I believe that one driving force for the reactions is the cracking of heptanes and higher paraffins to isopropyl and t-butyl cations which either alkylate methylcyclopentane/cyclohexane to form part of the fraction of 7 to 10 carbon atom-containing cyclohexanes or abstract hydride ion from methylcyclopentane to form propane, butane, and dimethyldecalins.

Examples 29-39 involve contacting batches of a hydrocarbon feed of 55.5 volume percent of methylcyclopentane and 44.5 volume percent of a heavy naphtha, with a single batch of catalyst comprising 30 grams of tantalum pentafluoride dissolved in 60 grams of hydrogen fluoride, in a stainless steel reactor at 25° C., under a hydrogen partial pressure of 2.04 atmospheres and under a total pressure of 3.04 atmospheres. The composition of the feed is given in Table IV. The heavy naphtha employed was a typical feed to a reformer and was a petroleum fraction which had been dehydrogenated and desulfurized. New charges of 132 grams of the feed were introduced into the reactor in Examples 29, 30, 32, 34, 36, and 38. Aliquots of the hydrocarbon layers were withdrawn in Examples 30, 32, 34, 36, and 38; and the entire remaining hydrocarbon layers were withdrawn in Examples 29, 31, 33, 35, 37, and 39.

The results in Table IV for Examples 29-39 are similar to those in Table III for Examples 15-28, with several important exceptions. The acyclic paraffins in the heavy naphtha portion of the feed in Examples 29-39 crack to form approximately equal concentrations of isobutane, on the one hand, and a mixture of pentanes and hexanes, on the other hand, whereas the acyclic paraffins in the light naphtha portion of the feed in Examples 15-28 crack to form propane and isobutane. Furthermore, when heavy naphtha is present, about 85 weight percent of the methylcyclopentane/cyclohexane is converted to dimethyldecalins while the remaining 15 weight percent is converted to cyclohexanes containing 7 to 10 carbon atoms. On the contrary, when light naphtha is present, only about 50 weight percent of the methylcyclopentane/cyclohexane is converted to dimethyldecalins while the remaining 50 weight percent is converted to cyclohexanes containing 7 to 10 carbon atoms. It is believed that the monocyclic naphthenes in light naphtha, heavy naphtha and total naphtha play an important role in the formation of upgraded products.

EXAMPLES 40-47

Continuous flow runs were made in a 75-milliliter Monel magnetically stirred reactor. The reactor was charged with tantalum pentafluoride, swept with nitrogen and then charged with hydrogen fluoride in the same manner as was the batch reactor employed in Examples 1-39 hereinabove. The temperature was also maintained as in Examples 1-39. The hydrocarbon feed was added continuously from the Ruska pump and the mixture was stirred. After the reactor became full with liquid, the entering feed displaced an equal volume of catalyst-hydrocarbon emulsion from the reactor into a settler. In the settler, the emulsion broke into two phases, with the heavier catalyst phase being withdrawn and returned to the reactor and the lighter hydrocarbon phase being withdrawn overhead and collected in a product receiver. The product was withdrawn from the receiver at intervals and analyzed by gas chromatography. The experimental parameters and results of Examples 40-47 are presented in Table V. Rates A and B and contact time in Table V have the same meanings as in Tables I-IV. Average catalyst age in Table V is the average age of catalyst in contact with the particular batch of hydrocarbon withdrawn from the reactor. Rate D in Table V is the rate of formation of all products expressed in units of grams of all products formed per hour per gram of tantalum pentafluoride.

Examples 40-47 involve the continuous addition of hydrocarbon feeds at a rate of 22.7 grams of the feed per hour to a catalyst system comprising 30 grams of tantalum pentafluoride dissolved in 30 grams of anhydrous hydrogen fluoride, at 25° C. and under a total pressure of 1 atmosphere. Examples 40-44 involve a hydrocarbon feed comprising 80 volume percent of methylcyclopentane and 20 volume percent of the light naphtha fraction employed in Examples 15-28.

TABLE V

| Example | 40 | 41 | 42 | 43 |
|---|---|---|---|---|
| Conditions | | | | |
| Sample Weight (g.) | 121 | 145 | 143 | 1368 |
| Contact Time (hrs.) | 21 | 27.7 | 35.2 | 99.1 |
| Average Catalyst Age (hrs.) | 10.5 | 24.4 | 31.6 | 67.2 |
| Results | | | | |
| Composition (Weight Percent) | | | | |

| | Feed | Product | | |
|---|---|---|---|---|
| propane | — | 0.9 | 1.1 | 1.1 | 0.3 |
| isobutane | — | 2.8 | 3.3 | 2.9 | 1.3 |
| isopentane | 0.1 | 0.7 | 1.2 | 0.8 | 0.6 |
| n-pentane | 0.3 | 0.0 | 0.1 | 0.3 | 0.1 |
| hexanes | 8.9 | 9.8 | 11.2 | 9.8 | 9.4 |
| methylcyclopentane | 83.3 | 8.9 | 10.5 | 9.5 | 14.0 |
| cyclohexane | 0.3 | 66.8 | 62.1 | 65.6 | 65.6 |
| branched C$_7$ paraffins | 3.7 | 1.6 | 1.7 | 1.7 | 2.9 |
| n-heptane | 1.1 | 0.1 | 0.3 | 0.3 | 0.6 |
| methylcyclohexane | 0.2 | 0.5 | 0.5 | 0.5 | 0.4 |
| branched C$_8$ paraffins | 1.6 | 0.0 | 0.0 | 0.0 | } 1.3 |
| C$_8$ cyclohexanes | — | 1.0 | 1.0 | 1.1 | |
| n-octane | 0.3 | 0.0 | 0.0 | 0.0 | 0.0 |
| C$_9$ paraffins | 0.4 | 0.0 | 0.0 | 0.0 | 0.0 |
| C$_9$ cyclohexanes | — | 1.4 | 1.5 | 1.5 | 0.6 |
| C$_{10}$ cyclohexanes | — | 0.0 | 0.1 | 0.1 | 0.0 |
| C$_{11}$ cyclohexanes | — | 0.0 | 0.0 | 0.0 | 0.0 |
| dimethyldecalins | — | 5.1 | 4.9 | 4.4 | 2.5 |
| higher | — | 0.3 | 0.3 | 0.4 | 0.3 |
| branched C$_{16}$ | — | — | — | — | — |
| n-hexadecane | — | — | — | — | — |
| Example No. | | 40 | 41 | 42 | 43 |

| Composition of Hexane Fraction (Weight Percent) | Feed | Product | | |
|---|---|---|---|---|
| 2,2-dimethylbutane | 3.5 | 55.2 | 48.9 | 46.0 | 21.3 |
| 2,3-dimethylbutane | 5.3 | 8.5 | 10.0 | 10.3 | 12.4 |
| 2-methylpentane | 29.4 | 21.2 | 23.7 | 24.8 | 32.6 |
| 3-methylpentane | 26.0 | 11.0 | 11.0 | 11.6 | 15.6 |
| n-hexane | 35.8 | 4.1 | 6.4 | 7.3 | 18.1 |
| Rate A | — | .080 | .115 | .085 | .035 |
| Rate B | — | .039 | .037 | .033 | .019 |
| Rate D | — | — | — | — | — |

| Example No. | 44 | 45 | 46 | 47 |
|---|---|---|---|---|
| Conditions | | | | |
| Sample Weight (g.) | 592 | 66 | 168 | 174 |
| Contact Time (hrs.) | 123.6 | 17.6 | 48.6 | 72.7 |
| Average Catalyst Age (hrs.) | 111.4 | 8.8 | 44.8 | 69.0 |
| Results | | | | |
| Composition (Weight Percent) | | Product | | |
| propane | 0.1 | 0.0 | 0.0 | 0.0 |
| isobutane | 0.5 | 0.2 | 0.2 | 0.1 |
| isopentane | 0.4 | 0.1 | 0.1 | 0.0 |
| n-pentane | 0.7 | — | — | — |
| hexanes | 9.2 | 1.3 | 0.7 | 0.5 |
| methylcyclopentane | 24.9 | 10.5 | 11.4 | 12.2 |

TABLE V-continued

| | | | | |
|---|---|---|---|---|
| cyclohexane | 56.2 | 76.1 | 76.0 | 76.9 |
| branched C$_7$ paraffins | 2.0 | — | — | — |
| n-heptane | 1.5 | — | — | — |
| methylcyclohexane | 0.3 | — | — | — |
| branched C$_8$ paraffins | 1.9 | — | — | — |
| C$_8$ cyclohexanes | | 0.1 | 0.1 | 0.0 |
| n-octane | 0.0 | — | — | — |
| C$_9$ paraffins | 0.0 | — | — | — |
| C$_9$ cyclohexanes | 0.4 | — | — | — |
| C$_{10}$ cyclohexanes | 0.0 | — | — | — |
| C$_{11}$ cyclohexanes | 0.0 | — | — | — |
| dimethyldecalins | 1.0 | 2.4 | 2.1 | 1.4 |
| higher | 0.1 | — | — | — |
| branched C$_{16}$ | — | 0.4 | 0.4 | 0.4 |
| n-hexadecane | — | 8.7 | 9.2 | 8.4 |
| higher | — | 0.1 | 0.0 | 0.0 |
| Example No. | 44 | 45 | 46 | 47 |

Composition of Hexane Fraction (Weight Percent)

| | Product | | | |
|---|---|---|---|---|
| 2,2-dimethylbutane | 7.9 | 49.9 | 50.3 | 43.0 |
| 2,3-dimethylbutane | 11.9 | 9.5 | 9.9 | 10.8 |
| 2-methylpentane | 36.3 | 25.2 | 26.7 | 30.1 |
| 3-methylpentane | 17.7 | 11.6 | 11.9 | 13.3 |
| n-hexane | 26.1 | 3.8 | 1.1 | 2.8 |
| Rate A | .023 | .029 | 0.23 | .007 |
| Rate B | .008 | .018 | .016 | .011 |
| Rate D | — | .031 | .024 | .015 |

The composition of the feed in Examples 40–44 is given in Table V. Examples 45–47 involve a hydrocarbon feed comprising 90 volume percent of methylcyclopentane and 10 volume percent of n-hexadecane.

The results in Table V for Examples 40–44 indicate that the presence of light naphtha in the feed results in about a 5-fold increase in the initial reaction rate but a more rapid decline in catalyst activity, relative to cases wherein the hydrocarbon feed does not contain the light naphtha fraction. The results in Table V for Examples 45–47 indicate that the presence of n-hexadecane has little effect on the initial reaction rate or on the rate of decline of catalyst activity relative to cases wherein hexadecane is not present in the hydrocarbon feed.

EXAMPLE 48

Following essentially the procedure of Examples 1–39, the isomerization of other dimethyldecalin isomers to 2,6-dimethyldecalin was carried out in a 300-milliliter, magnetically stirred, stainless steel reactor. The reactor was charged with 20 grams of tantalum pentafluoride and 80 grams of hydrogen fluoride and was stirred under a hydrogen partial pressure of 0.68 atmosphere and maintained at a temperature of −23° C. and a total pressure of 1.68 atmospheres. About 18 grams of a fraction comprising mainly mixed dimethyldecalin isomers and boiling between 215° C. and 225° C. was added. The temperature of the reaction mixture rose immediately above 10° C. due to the heat of isomerization and crystallization and, after about 15 minutes, dropped back to −23° C. The isomerization reaction was apparently complete in less than 15 minutes but stirring at −23° C. was continued for a total of 24 hours. At this time, 100 milliliters of water was added to quench the catalyst and terminate the reaction. The temperature was raised to 50° C. to melt the 2,6-dimethyldecalin. The reactor contents were withdrawn through a standpipe.

TABLE VI

| | Composition (Weight Percent) | | |
|---|---|---|---|
| Component | Feed | Product | C$_{12}$ Product Fraction |
| C$_6$—C$_8$ paraffins and naphthenes | 1.9 | 0.9 | — |
| C$_9$—C$_{10}$ paraffins and naphthenes | 2.6 | 2.0 | — |
| 2-ethyldecalin | 0.5 | 0.0 | 0.0 |
| 2,6-dimethyldecalin | 51.1 | 85.4 | 94.7 |
| 2,7-dimethyldecalin | | 4.6 | 4.1 |
| other dimethyldecalins | 36.9 | | |
| hexadecane | 7.0 | 6.1 | — |

About 25 milliliters of benzene was added to keep the hydrocarbon product liquid. It was then separated from the aqueous acid phase, washed with water and analyzed by gas chromatography. The benzene was then allowed to evaporate, leaving a white crystalline solid residue. The melting point of the remaining solid, 45°–46° C., indicates it to be almost 100 percent pure 2,6-dimethyldecalin. The results of Example 48 are presented in Table VI.

EXAMPLE 49

367 grams of the combined products of Examples 2, 3 and 5 were diluted with 2000 grams of benzene, and the resulting mixture was dehydrogenated over a chromiar-henia-on-alkalized-alumina catalyst at atmospheric pressure and 525° C. The liquid and gaseous products were collected, measured and analyzed. The results are presented in Table VII.

EXAMPLE 50

A desulfurized and hydrogenated heavy naphtha boiling in the range of 180° C. to 250° C. containing dicyclic naphthenic components having 12 carbon atoms and associated paraffins, was treated using the procedure of Examples 40–47 with a catalyst 40 grams of of hydrogen fluoride and 37.7 grams of tantalum pentafluoride at 25° C. at a WHSV of 0.76 grams of naphtha per gram of tantalum pentafluoride per hour and under a partial pressure of 40.8 atmospheres of hydrogen and a total pressure of 41.8 atmospheres. The paraffins were hydrocracked to a mixture of paraffinic products containing 4 to 6 carbon atoms and the bicyclic naphthenic components were isomerized to the equilibrium mixture of dimethyldecalins. A cut of the product weighing 18 grams and comprising mainly the equilibrated mixture of dimethyldecalins and boiling in the range of 215° C. to 225° C. was contacted with a catalyst comprising 80 grams of hydrogen fluoride and 20 grams of tantalum pentafluoride at −23° C. in an autoclave under 0.68 atmosphere of partial pressure of hydrogen and a total pressure of 1.68 atmospheres.

TABLE VII

| | Composition (Weight Percent) | |
|---|---|---|
| Component | Feed | Product |
| C$_4$—C$_5$ | 1.0 | 0.3 |
| hexanes | 3.8 | 4.5 |
| methylcyclopentanes | 9.6 | 8.1 |
| cyclohexane | 71.9 | 27.0 |

TABLE VII-continued

| Component | Composition (Weight Percent) | |
|---|---|---|
| | Feed | Product |
| methylcyclohexane | 0.2 | 1.9 |
| C$_8$ naphthenes | 1.8 | 3.5 |
| C$_9$ naphthenes | 0.2 | 0.1 |
| C$_{10}$ naphthenes | 0.1 | 0.1 |
| C$_{11}$ naphthenes | 0.01 | 0.0 |
| dimethyldecalins | 10.3 | 1.0 |
| higher | 1.1 | 0.0 |
| aromatics | | |
| benzene | 0.0 | 33.7 |
| toluene | — | 0.9 |
| C$_8$ | 0.0 | 2.6 |
| C$_9$ | 0.0 | 0.7 |
| C$_{10}$ | 0.0 | 0.1 |
| naphthalene | 0.0 | 0.2 |
| methylnaphthalenes | 0.0 | 1.7 |
| dimethylnaphthalenes | 0.0 | 12.5 |
| higher | 0.0 | 0.9 |
| Composition of C$_8$ Aromatics Fraction (Weight Percent) | | |
| ethylbenzene | 0.0 | 1 |
| p-xylene | 0.0 | 33 |
| m-xylene | 0.0 | 55 |
| o-xylene | 0.0 | 11 |
| Composition of C$_9$ Aromatics Fraction (Weight Percent) | | |
| mesitylene | 0.0 | 14 |
| pseudocumene | 0.0 | 68 |
| hemimellitene | 0.0 | 13 |
| others | 0.0 | 5 |
| Composition of Methylnaphthalene Fraction (Weight Percent) | | |
| beta-methylnaphthalene | 0.0 | 91 |
| alpha-methylnaphthalene | 0.0 | 9 |
| Composition of C$_{12}$ Naphthalenes Fraction (Weight Percent) | | |
| ethylnaphthalenes | 0.0 | 2 |
| 2,6- and 2,7-dimethyl-naphthalene | 0.0 | 60 |
| other dimethyl-naphthalenes | 0.0 | 38 |

After 24 hours, 100 milliliters of water was added to neutralize the catalyst and terminate the reaction. The temperature was raised to 50° C. to melt the crystallized solid and the product was withdrawn. Gas chromatographic analysis of the product indicated it to be 95 percent by weight of trans-2-syn-6-syn-dimethyldecalin with about 5 weight percent of dimethyldecalin isomers other than 2,6-dimethyldecalin.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. A process for preparing 2,6-dimethyldecalin comprising contacting one or more 12 carbon atom-containing dicyclic naphthenic isomers of 2,6-dimethyldecalin with an isomerization catalyst system comprising a solution of tantalum pentafluoride or niobium pentafluoride or both in hydrogen fluoride at a temperature in the range of from about −60° C. to about 90° C. and in the presence of hydrogen, to thereby isomerize the dicyclic naphthenic isomer or isomers to 2,6-dimethyldecalin.

2. The process of claim 1 wherein the isomerization is performed at a hydrogen partial pressure in the range of from about 0.07 to about 82 atmospheres and a WHSV in the range of from about 0.1 to about 2 grams of the dicyclic naphthenic isomer or isomers per gram of the metal pentafluoride in the isomerization catalyst system per hour and the weight ratio of the pentafluoride to the hydrogen fluoride in the isomerization catalyst system is in the range of from about 0.1 to about 2.

3. The process of claim 1 wherein the isomerization is performed at a temperature above −10° C. and the 2,6-dimethyldecalin formed is subsequently crystallized at a temperature within the range of from about −60° C. to about −10° C.

4. The process of claim 1 wherein the isomerization is performed at a temperature in the range of from about −60° C. to about −10° C., a WHSV in the range of from about 0.1 to about 0.5 grams of the dicyclic naphthenic isomer or isomers per gram of the metal pentafluoride in the isomerization catalyst system per hour, and a weight ratio of the pentafluoride to the hydrogen fluoride in the isomerization catalyst system in the range of from about 0.1 to about 0.5, and 2,6-dimethyldecalin crystallizes as it is formed.

5. The process of claims 3 or 4 wherein the amount of 2,6-dimethyldecalin which crystallizes is equivalent to at least 85 weight percent of the total amount of 12 carbon atom-containing dicyclic naphthenes in the feed.

6. The process of claims 3 or 4 wherein a hydrocarbon feed comprising 12 carbon atom-containing dicyclic naphthenes at a total concentration of at least about 80 weight percent is contacted with the isomerization catalyst system to thereby form 2,6-dimethyldecalin, being substantially free of amounts of sulfur-containing compounds and aromatic and other unsaturated hydrocarbons sufficient to deactivate the isomerization catalyst system, and the 12 carbon atom-containing dicyclic naphthenes comprising the 12 carbon atom-containing dicyclic naphthenic isomer or isomers of 2,6-dimethyldecalin.

7. The process of claim 6 wherein the hydrocarbon feed boils in the range of from about 210° C. to about 230° C.

8. The process of claim 6 wherein tantalum pentafluoride is employed in the isomerization catalyst system.

9. The process of claim 1 wherein the 2,6-dimethyldecalin produced is subsequently dehydrogenated to form 2,6-dimethylnaphthalene.

10. The process of claim 1 wherein the 12 carbon atom-containing dicyclic naphthenic isomer or isomers of 2,6-dimethyldecalin are prepared by a process comprising contacting a hydrocarbon solution comprising at least 40 to 100 weight percent of methylcyclopentane, cyclohexane or both with a dimerization catalyst system comprising a solution of tantalum pentafluoride or niobium pentafluoride or both in hydrogen fluoride at a temperature in the range of from about 10° C. to about 90° C. and in the presence of hydrogen at a partial pressure in the range of from about 0.7 to about 20 atmospheres, the hydrocarbon solution being substantially free of amounts of sulfur-containing compounds and aromatic and other unsaturated organic compounds sufficient to deactivate the dimerization catalyst system, the weight ratio of the pentafluoride to the hydrogen fluoride in the dimerization catalyst system being in the range of from about 0.1 to about 2, to thereby dimerize the methylcyclopentane or cyclohexane or both to form a hydrocarbon product mixture comprising the 12 carbon atom-containing dicyclic naphthenic isomer or isomers of 2,6-dimethyldecalin.

11. The process of claim 10 wherein the dimerization is performed at a WHSV in the range of from about 0.1 to about 7 grams of the hydrocarbon solution per gram of the metal pentafluoride in the dimerization catalyst system per hour.

12. The process of claim 10 wherein the hydrocarbon solution contains a total concentration of from about 50 to about 85 weight percent of methylcyclopentane or cyclohexane or both.

13. The process of claim 10 wherein the hydrocarbon solution boils in the range of from about 30° C. to about 230° C.

14. The process of claim 10 wherein the hydrocarbon solution comprises from about 15 to about 60 weight percent of acyclic paraffins boiling in the range of from about 30° C. to about 230° C.

15. The process of claim 10 wherein the hydrocarbon solution comprises naphtha, and the naphtha is upgraded by hydrocracking and isomerization reactions.

16. The process of claim 10 wherein tantalum pentafluoride is employed in the dimerization catalyst system.

17. The process of claim 10 wherein the hydrocarbon product mixture is separated from the dimerization catalyst system and a fraction of the hydrocarbon product mixture comprising the aforesaid 12 carbon atom-containing dicyclic naphthenic isomer or isomers is separated.

18. The process of claim 6 wherein the hydrocarbon feed is prepared by contacting a hydrocarbon starting material containing a total concentration of 12 carbon atom-containing dicyclic naphthenes of at least about 5 weight percent with the isomerization catalyst system, in the presence of hydrogen and at a temperature in the range of from about 10° C. to about 90° C., the starting material being substantially free of sulfur-containing compounds and aromatic and other unsaturated organic compounds sufficient to deactivate the isomerization catalyst system, to thereby form a hydrocarbon mixture comprising the hydrocarbon feed; separating the hydrocarbon product mixture from the dimerization catalyst system; and separating a fraction comprising the hydrocarbon feed from the hydrocarbon product mixture.

19. The process of claim 18 wherein the hydrocarbon starting material contains a total concentration of 12 carbon atom-containing dicyclic naphthenes of at least about 10 weight percent.

20. The process of claim 18 wherein the hydrocarbon starting material comprises acyclic paraffins which are upgraded by hydrocracking and isomerization reactions.

21. The process of claim 18 wherein the hydrocarbon starting material comprises naphtha which is upgraded by hydrocracking and isomerization reactions.

22. A process for preparing at least one 12 carbon atom-containing dicyclic naphthene comprising contacting a hydrocarbon solution comprising at least 40 to 100 weight percent of methylcyclopentane, cyclohexane or both with a dimerization catalyst system comprising a solution of tantalum pentafluoride or niobium pentafluoride or both in hydrogen fluoride at a temperature in the range of from about 10° C. to about 90° C. and in the presence of hydrogen at a partial pressure in the range of from about 0.7 to about 20 atmospheres, the hydrocarbon solution being substantially free of amounts of sulfur-containing compounds and aromatic and other unsaturated organic compounds sufficient to deactivate the catalyst system, the weight ratio of the pentafluoride to the hydrogen fluoride in the dimerization catalyst system being in the range of from about 0.1 to about 2, to thereby dimerize the methylcyclopentane or cyclohexane or both to form a hydrocarbon product mixture comprising at least 12 carbon atom-containing dicyclic naphthene.

23. The process of claim 22 wherein the dimerization is performed at a WHSV in the range of from about 0.1 to about 7 grams of the hydrocarbon solution per gram of the metal pentafluoride in the dimerization catalyst system per hour.

24. The process of claim 22 wherein the hydrocarbon solution contains a total concentration of from about 50 to about 85 weight percent of methylcyclopentane or cyclohexane or both.

25. The process of claim 26 wherein the hydrocarbon solution boils in the range of from about 30° C. to about 230° C.

26. The process of claim 22 wherein the hydrocarbon solution comprises from about 15 to about 60 weight percent of acyclic paraffins, boiling in range of from about 30° C. to about 230° C.

27. The process of claim 22 wherein the hydrocarbon solution comprises naphtha, and the naphtha is upgraded by hydrocracking and isomerization to products of higher octane value.

28. The process of claim 22 wherein tantalum pentafluoride is employed in the dimerization catalyst system.

29. The process of claim 22 wherein the hydrocarbon product mixture is separated from the dimerization catalyst system and a fraction of the hydrocarbon product mixture comprising the 12 carbon atom-containing dicyclic naphthenes is separated.

* * * * *

UNITED STATES PATENT AND TRADEMARK OFFICE
CERTIFICATE OF CORRECTION

PATENT NO. : 4,300,008

DATED : November 10, 1981

INVENTOR(S) : David A. McCaulay

It is certified that error appears in the above-identified patent and that said Letters Patent is hereby corrected as shown below:

| Column | Line | |
|---|---|---|
| 1 | 26 | "2.6" should be -- 2,6 --. |
| 9 | 64-5 | "methylcyclopentane" should be -- methylcyclopentene --. |
| 10 | 63 | "catatalyst" should be -- catalyst --. |
| 10 | 64 | "contained" should be -- obtained --. |
| 11 | 22 | "methcyclopentane" should be -- methylcyclopentane --. |
| 14 | 56 | "215°OC." should be -- 215°C. --. |
| 18 | Table III, Example No. 19-23 | methylcyclohexane "1.2  0.9  1.1  1.9  blank" should be methylcyclohexane -- 1.2  blank  0.9  1.1  1.9 --. |

UNITED STATES PATENT AND TRADEMARK OFFICE
CERTIFICATE OF CORRECTION

PATENT NO. : 4,300,008
DATED : November 10, 1981
INVENTOR(S) : David A. McCaulay It is certified that error appears in the above-identified patent and that said Letters Patent is hereby corrected as shown below:

| Column | Line | |
|---|---|---|
| 19 | Table IV, No. 29-32 | $C_8$ cyclopentanes<br>"0.0   0.0   0.0   0.0   blank"<br>should be<br>Table IV, No. 27<br>$C_8$ cyclopentanes<br>-- blank   0.0   0.0   0.0   0.0 --. |
| 21 | 31 | "rate C" should be -- Rate C --. |
| 21 | 50 | "rate" should be -- Rate --. |
| 22 | 54 | "indicates" should be -- indicate --. |
| 22 | 55 | "recited" should be -- reacted --. |
| 23 | 56-7 | "pha-" (improperly hyphenated) should be -- phases --. |
| 24 | Table V | "Example" should be -- Example No. --. |

UNITED STATES PATENT AND TRADEMARK OFFICE
CERTIFICATE OF CORRECTION

PATENT NO. : 4,300,008
DATED : November 10, 1981
INVENTOR(S) : David A. McCaulay Page 3 of 3

It is certified that error appears in the above-identified patent and that said Letters Patent is hereby corrected as shown below:

| Column | Line | |
|--------|------|---|
| 24 | 43 | Example No. & numbers should not be repeated. |
| 25 | 18 | Example No. & numbers should not be repeated. |
| 24 | 58 | "72.7" should be under Ex. 47. |
| 24 | 59 | "69.0" should be under Ex. 47. |
| 24 | 65 | "0.1" should be under Ex. 45 and other numbers moved over. |
| 25 | 28 | "0.23" should be -- .023 --. |
| 26 | 14 | "94.7" should be -- 94.9 --. |

Signed and Sealed this

Thirty-first Day of August 1982

[SEAL]

Attest:

GERALD J. MOSSINGHOFF

*Attesting Officer*  *Commissioner of Patents and Trademarks*